United States Patent
Cosford et al.

(10) Patent No.: US 7,371,767 B2
(45) Date of Patent: May 13, 2008

(54) HETEROARYL SUBSTITUTED PYRROLE MODULATORS OF METABOTROPIC GLUTAMATE RECEPTOR-5

(75) Inventors: Nicholas D. P. Cosford, San Diego, CA (US); Dehua Huang, San Diego, CA (US); Nicholas D. Smith, San Diego, CA (US)

(73) Assignee: Merck & Co., Inc., Rahway, NJ (US)

( * ) Notice: Subject to any disclaimer, the term of this patent is extended or adjusted under 35 U.S.C. 154(b) by 595 days.

(21) Appl. No.: 10/499,393

(22) PCT Filed: Dec. 17, 2002

(86) PCT No.: PCT/US02/40486

§ 371 (c)(1), (2), (4) Date: Jun. 17, 2004

(87) PCT Pub. No.: WO03/059904

PCT Pub. Date: Jul. 24, 2003

(65) Prior Publication Data

US 2005/0085514 A1    Apr. 21, 2005

Related U.S. Application Data

(60) Provisional application No. 60/343,262, filed on Dec. 21, 2001.

(51) Int. Cl.
*A61K 31/4433* (2006.01)
*A61K 31/427* (2006.01)
*C07D 277/32* (2006.01)
*C07D 231/14* (2006.01)
*C07D 207/325* (2006.01)

(52) U.S. Cl. .............. 514/340; 514/340; 514/365; 514/422; 546/268.1; 548/146; 548/373.1; 548/518

(58) Field of Classification Search .......... 546/268.1; 548/518, 146, 373.1; 544/333; 514/340, 514/422, 365
See application file for complete search history.

(56) References Cited

OTHER PUBLICATIONS

CAPLUS Accession No. 1995:441009, abstract of Oishi et al journal article, Chemical & Pharm. Bulletin (1994), vol. 42(11), pp. 2219-2224.*
Abstract of: Reiman, E., et al., "Intramolecular Alkylation of Aromatic Compounds. Part XXXIV. Synthesis of (Pyridinyl) Indoles as Potential Precursors to Ergolines", Pharmazie (2000) vol. 55, No. 12 pp. 907-912.

* cited by examiner

*Primary Examiner*—Kamal A. Saeed
*Assistant Examiner*—Janet L. Coppins
(74) *Attorney, Agent, or Firm*—J. Eric Thies; William Krovatin

(57) ABSTRACT

Pyrrole compounds substituted directly, or by a bridge, with a heteroaryl moiety containing N adjacent to the point of connection of the heteroaryl, are mGluR5 modulators useful in the treatment of psychiatric and mood disorders such as, for example, schizophrenia, anxiety, depression, bipolar disorder and panic, as well as in the treatment of pain, circadian rhythm disorders, and other diseases.

16 Claims, No Drawings

HETEROARYL SUBSTITUTED PYRROLE MODULATORS OF METABOTROPIC GLUTAMATE RECEPTOR-5

RELATED APPLICATION DATA

This is a National filing under 35 USC 371 of PCT/US 02/40486, filed Dec. 17, 2002, which claims priority from U.S. Ser. No. 60/343,262, filed Dec. 21, 2001.

BACKGROUND OF THE INVENTION

1. Field of the Invention

The present invention is directed to pyrrole compounds substituted with a heteroaryl moiety. In particular, this invention is directed to pyrrole compounds substituted directly, or by a bridge, with a heteroaryl moiety containing N adjacent to the point of connection of the heteroaryl which are metabotropic glutamate receptor—subtype 5 ("mGluR5") modulators useful in the treatment of psychiatric and mood disorders such as, for example, schizophrenia, anxiety, depression, panic, bipolar disorder, and circadian rhythm disorders, as well as in the treatment of pain, Parkinson's disease, cognitive dysfunction, epilepsy, drug addiction, drug abuse, drug withdrawal and other diseases.

2. Related Background

A major excitatory neurotransmitter in the mammalian nervous system is the glutamate molecule, which binds to neurons, thereby activating cell surface receptors. Such surface receptors are characterized as either ionotropic or metabotropic glutamate receptors. The metabotropic glutamate receptors ("mGluR") are G protein-coupled receptors that activate intracellular second messenger systems when bound to glutamate. Activation of mGluR results in a variety of cellular responses. In particular, mGluR1 and mGluR5 activate phospholipase C, which is followed by mobilizing intracellular calcium.

Modulation of metabotropic glutamate receptor subtype 5 (mGluR5) is useful in the treatment of diseases that affect the nervous system (see for example W. P. J. M Spooren et al., *Trends Pharmacol. Sci.*, 22:331-337 (2001) and references cited therein). For example, recent evidence demonstrates the involvement of mGluR5 in nociceptive processes and that modulation of mGluR5 using mGluR5-selective compounds is useful in the treatment of various pain states, including acute, persistent and chronic pain [K Walker et al., *Neuropharmacology*, 40: 1-9 (2001); F. Bordi, A. Ugolini *Brain Res.*, 871:223-233 (2001)], inflammatory pain [K Walker et al., *Neuropharmacology*, 40:10-19 (2001); Bhave et al. *Nature Neurosci.* 4:417-423 (2001)] and neuropathic pain [Dogrul et al. *Neurosci. Lett.* 292:115-118 (2000)].

Further evidence supports the use of modulators of mGluR5 in the treatment of psychiatric and neurological disorders. For example, mGluR5-selective compounds such as 2-methyl-6-(phenylethynyl)-pyridine ("MPEP") are effective in animal models of mood disorders, including anxiety and depression [W. P. J. M Spooren et al., *J. Pharmacol. Exp. Ther.*, 295:1267-1275 (2000); E. Tatarczynska et al, *Brit. J. Pharmacol.*, 132:1423-1430 (2001); A. Klodzynska et al, *Pol. J. Pharmacol.*, 132:1423-1430 (2001)]. Gene expression data from humans indicate that modulation of mGluR5 may be useful for the treatment of schizophrenia [T. Ohnuma et al, *Mol. Brain. Res.*, 56:207-217 (1998); ibid, *Mol. Brain. Res.*, 85:24-31 (2000)]. Studies have also shown a role for mGluR5, and the potential utility of mGluR5-modulatory compounds, in the treatment of movement disorders such as Parkinson's disease [W. P. J. M Spooren et al., *Europ. J. Pharmacol.* 406:403-410 (2000); H. Awad et al., *J. Neurosci.* 20:7871-7879 (2000); K. Ossawa et al. *Neuropharmacol.* 41:413-420 (2001)]. Other research supports a role for mGluR5 modulation in the treatment of cognitive dysfunction [G. Riedel et al, *Neuropharmacol.* 39:1943-1951 (2000)], epilepsy [A. Chapman et al, *Neuropharmacol.* 39:1567-1574 (2000)] and neuroprotection [V. Bruno et al, *Neuropharmacol.* 39:2223-2230 (2000)]. Studies with mGluR5 knockout mice and MPEP also suggest that modulation of these receptors may be useful in the treatment of drug addiction, drug abuse and drug withdrawal [C. Chiamulera et al. *Nature Neurosci.* 4:873-874 (2001)].

International Patent Publication WO 01/12627 and WO 99/26927 describe heteropolycyclic compounds and their use as metabotropic clutamate receptor antagonists.

Compounds that include ringed systems are described by various investigators as effective for a variety of therapies and utilities. For example, International Patent Publication No. WO 98/25883 describes ketobenzamides as calpain inhibitors, European Patent Publication No. EP 811610 and U.S. Pat. Nos. 5,679,712, 5,693,672 and 5,747,541 describe substituted benzoylguanidine sodium channel blockers, and U.S. Pat. No. 5,736,297 describes ring systems useful as a photosensitive composition.

However, there remains a need for novel compounds and compositions that therapeutically inhibit mGluR5 with minimal side effects.

SUMMARY OF THE INVENTION

The present invention is directed to novel pyrrole compounds substituted directly, or by a bridge, with a heteroaryl moiety containing N adjacent to the point of connection of the heteroaryl, are mGluR5 modulators useful in the of psychiatric and mood disorders such as, for example, schizophrenia, anxiety, depression, panic, bipolar disorder, and circadian rhythm and sleep disorders—such as shift-work induced sleep disorder or jet-lag, as well as in the treatment of pain, Parkinson's disease, cognitive dysfunction, epilepsy, drug addiction, drug abuse, drug withdrawal and other diseases. This invention also provides a pharmaceutical composition which includes an effective amount of the novel pyrrole compounds substituted with a heteroaryl moiety, and a pharmaceutically acceptable carrier.

This invention further provides a method of treatment of psychiatric and mood disorders such as, for example, schizophrenia, anxiety, depression, panic, bipolar disorder, and circadian rhythm and sleep disorders—such as shift-work induced sleep disorder or jet-lag, as well as a method of treatment of pain, Parkinson's disease, cognitive dysfunction, epilepsy, drug addiction, drug abuse and drug withdrawal by the administration of an effective amount of the novel pyrrole compounds substituted with a heteroaryl moiety.

DETAILED DESCRIPTION OF THE INVENTION

A compound represented by Formula (I):

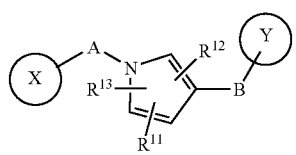

(I)

or a pharmaceutically acceptable salt thereof, wherein

X and Y each independently is aryl or heteroaryl wherein at least one of X and Y is a heteroaryl with N adjacent to the position of attachment to A or B respectively;

X is optionally substituted with 1-7 independent halogen, —CN, $NO_2$, —$C_{1-6}$aklyl, —$C_{1-6}$alkenyl, —$C_{1-6}$alkynyl, —$OR^1$, —$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —$C(=NR^1)R^2$, or —$C(=NOR^1)R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —$O(C_{0-6}$alkyl), —$O(C_{3-7}$cycloalkyl), —O(aryl), —O(heteroaryl), —$N(C_{0-6}$alkyl)($C_{0-6}$alkyl), —$N(C_{0-6}$alkyl)($C_{3-7}$cycloalkyl), or —$N(C_{0-6}$alkyl)(aryl) groups;

$R^1$, $R^2$, and $R^3$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —$O(C_{0-6}$alkyl), —$O(C_{3-7}$cycloalkyl), —O(aryl), —O(heteroaryl), —$N(C_{0-6}$alkyl)($C_{0-6}$alkyl), —$N(C_{0-6}$alkyl)($C_{3-7}$cycloalkyl), —$N(C_{0-6}$alkyl)(aryl) substituents;

$R^4$ is —$C_{1-6}$alkyl, —$C_{3-7}$cycloalkyl, heteroaryl, or aryl; optionally substituted with 1-5 independent halogen, —CN, —$C_{1-6}$alkyl, —$O(C_{0-6}$alkyl), —$O(C_{3-7}$cycloalkyl), —O(aryl), —O(heteroaryl), —$N(C_{0-6}$alkyl)($C_{0-6}$alkyl), —$N(C_{0-6}$alkyl)($C_{3-7}$cycloalkyl), —$N(C_{0-6}$alkyl)(aryl) substituents;

A is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^9$CO—$C_{0-2}$alkyl-, —$C_{0-2}$alkyl-$NR^9SO_2$—$C_{0-2}$alkyl- or -hetero$C_{0-4}$alkyl;

Y is optionally substituted with 1-7 independent halogen, —CN, $NO_2$, —$C_{1-6}$alkyl, —$C_{1-6}$alkenyl, —$C_{1-6}$alkyl, —$OR^5$, —$NR^5R^6$, —$C(=NR^5)NR^6R^7$, —$N(=NR^5)NR^6R^7$, —$NR^5COR^6$, —$NR^5CO_2R^6$, —$NR^5SO_2R^8$, —$NR^5CONR^6R^7$, —$SR^8$, —$SOR^8$, —$SO_2R^8$, —$SO_2NR^5R^6$, —$COR^5$, —$CO_2R^5$, —$CONR^5R^6$, —$C(=NR^5)R^6$, or —$C(=NOR^5)R^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —$O(C_{0-6}$alkyl), —$O(C_{3-7}$cycloalkyl), —O(aryl), —O(heteroaryl), —$N(C_{0-6}$alkyl)($C_{0-6}$alkyl), —$N(C_{0-6}$alkyl)($C_{3-7}$cycloalkyl), or —$N(C_{0-6}$alkyl)(aryl) groups;

$R^5$, $R^6$, and $R^7$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —$O(C_{0-6}$alkyl), —$O(C_{3-7}$cycloalkyl), —O(aryl), —O(heteroaryl), —$N(C_{0-6}$alkyl)($C_{0-6}$alkyl), —$N(C_{0-6}$alkyl)($C_{3-7}$cycloalkyl), —$N(C_{0-6}$alkyl)(aryl) substituents;

$R^8$ is —$C_{1-6}$alkyl, —$C_{3-7}$cycloalkyl, heteroaryl, or aryl; optionally substituted with 1-5 independent halogen, —CN, —$C_{1-6}$alkyl, —$O(C_{0-6}$alkyl), —$O(C_{3-7}$cycloalkyl), —O(aryl), —O(heteroaryl), —$N(C_{0-6}$alkyl)($C_{0-6}$alkyl), —$N(C_{0-6}$alkyl)($C_{3-7}$cycloalkyl), —$N(C_{0-6}$alkyl)(aryl) substituents;

B is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$CO_{0-2}$alkyl-, —$C_{0-2}$alkyl-$NR^{10}$CO—$C_{0-2}$alkyl-, —$C_{0-2}$alkyl-$NR^{10}SO_2$—$C_{0-2}$alkyl- or -hetero$C_{0-4}$alkyl;

$R^9$ and $R^{10}$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —$O(C_{0-6}$alkyl), —$O(C_{3-7}$cycloalkyl), —O(aryl), —O(heteroaryl), —$N(C_{0-6}$alkyl)($C_{0-6}$alkyl), —$N(C_{0-6}$alkyl)(aryl) substituents;

$R^{11}$, $R^{12}$ and $R^{13}$ is each independently halogen, —$C_{0-6}$alkyl, $C_{0-6}$alkoxyl, =O, =$N(C_{0-4}$alkyl), or —$N(C_{0-4}$alkyl)($C_{0-4}$alkyl), wherein optionally two of $R^{11}$, $R^{12}$ and $R^{13}$ are combined to form a cycloalkyl, heterocycloalkyl, aryl or heteroaryl ring fused to the pyrrole moiety; wherein the —$C_{1-6}$alkyl substituent, cycloalkyl ring, or heterocycloalkyl ring each optionally is further substituted with 1-5 independent halogen, —CN, —$C_{1-6}$alkyl, —$O(C_{0-6}$alkyl), —$O(C_{3-7}$cycloalkyl), —O(aryl), —O(heteroaryl), —$N(C_{0-6}$alkyl)($C_{0-6}$alkyl), —$N(C_{0-6}$alkyl)($C_{3-7}$cycloalkyl), or —$N(C_{0-6}$alkyl)(aryl) groups;

any N may be an N-oxide; and wherein any of the alkyl optionally is substituted with 1-9 independent halogens.

In one aspect, the compound of this invention is represented by Formula (I) or a pharmaceutically acceptable salt thereof, wherein X is 2-pyridyl optionally substituted with 1-4 independent halogen, —CN, $NO_2$, —$C_{1-6}$alkyl, —$C_{1-6}$alkenyl, —$C_{1-6}$alkynyl, —$OR^1$, —$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —$C(=NR^1)R^2$, or —$C(=NOR^1)R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —$O(C_{0-6}$alkyl), —$O(C_{3-7}$cycloalkyl), —O(aryl), —O(heteroaryl), —$N(C_{0-6}$alkyl)($C_{0-6}$alkyl), —$N(C_{0-6}$alkyl)($C_{3-7}$cycloalkyl), or —$N(C_{0-6}$alkyl)(aryl) groups;

$R^1$, $R^2$, and $R^3$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —($C_{0-6}$alkyl), —($C_{3-7}$cycloalkyl), —O(aryl), —O(heteroaryl), —$N(C_{0-6}$alkyl)($C_{0-6}$alkyl), —$N(C_{0-6}$alkyl)($C_{3-7}$cycloalkyl), —$N(C_{0-6}$alkyl)(aryl) substituents;

$R^4$ is —$C_{1-6}$alkyl, —$C_{3-7}$cycloalkyl, heteroaryl, or aryl; optionally substituted with 1-5 independent halogen, —CN, —$C_{1-6}$alkyl, —$O(C_{0-6}$alkyl), —($C_{3-7}$cycloalkyl), —O(aryl), (heteroaryl), —$N(C_{0-6}$alkyl)($C_{0-6}$alkyl), —$N(C_{0-6}$alkyl)($C_{3-7}$cycloalkyl), —$N(C_{0-6}$alkyl)(aryl) substituents;

A is —$C_{0-4}$alkyl, —$C_{0-2}$alkyl-SO—$C_{0-2}$alkyl-, —$C_{0-2}$alkyl-$SO_2$—CO-2alkyl-, —$C_{0-2}$alkyl-CO—$C_{0-2}$alkyl-, —$C_{0-2}$alkyl-$NR^9$CO—$C_{0-2}$alkyl-, —$C_{0-2}$alkyl-$NR^9SO_2$—$C_{0-2}$alkyl- or -hetero$C_{0-4}$alkyl;

Y is aryl or heteroaryl optionally substituted with 1-7 independent halogen, —CN, $NO_2$, —$C_{1-6}$alkyl, —$C_{1-6}$alkenyl, —$C_{1-6}$alkynyl, —$OR^5$, —$NR^5R^6$, —$C(=NR^5)NR^6R^7$, —$N(=NR^5)NR^6R^7$, —$NR^5COR^6$, —$NR^5CO_2R^6$, —$NR^5SO_2R^8$, —$NR^5CONR^6R^7$, —$SR^8$, —$SOR^8$, —$SO_2R^8$, —$SO_2NR^5R^6$, —$COR^5$, —$CO_2R^5$, —$CONR^5R^6$, —$C(=NR^5)R^6$, or —$C(=NOR^5)R^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —$O(C_{0-6}$alkyl), —$O(C_{3-7}$cycloalkyl), —O(aryl), —O(heteroaryl), —$N(C_{0-6}$alkyl)($C_{0-6}$alkyl), —$N(C_{0-6}$alkyl)($C_{3-7}$cycloalkyl), or —$N(C_{0-6}$alkyl)(aryl) groups;

$R^5$, $R^6$, and $R^7$ each independently is —$C_{0-6}$alkyl, —$C_{3-7}$cycloalkyl, heteroaryl, or aryl; any of which is optionally substituted with 1-5 independent halogen, —CN, —$C_{1-6}$ alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^8$ is —$C_{1-6}$alkyl, —$C_{3-7}$cycloalkyl, heteroaryl, or aryl; optionally substituted with 1-5 independent halogen, —CN, —$C_{1-6}$alkyl, —O($C_{0-6}$alkyl), —($C_{3-7}$ cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

B is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^{10}$CO—$C_{0-2}$alkyl-, —$C_{0-2}$alkyl-$NR^{10}SO_2$—$C_{0-2}$alkyl- or -hetero$C_{0-4}$alkyl;

$R^9$ and $R^{10}$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^{11}$, $R^{12}$ and $R^{13}$ is each independently halogen, —$C_{0-6}$alkyl, —$C_{0-6}$alkoxyl, =O, =N($C_{0-4}$alkyl), or —N($C_{0-4}$alkyl)($C_{0-4}$-alkyl), wherein optionally two of $R^{11}$, $R^{12}$ and $R^{13}$ are combined to form a cycloalkyl, heterocycloalkyl, aryl or heteroaryl ring fused to the pyrrole moiety; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

any N may be an N-oxide; and wherein any of the alkyl optionally is substituted with 1-9 independent halogens.

In an embodiment of this one aspect, the compound of this invention is represented by Formula (I) or a pharmaceutically acceptable salt thereof, wherein X is 2-pyridyl optionally substituted with 1-4 independent halogen, —CN, $NO_2$, —$C_{1-6}$alkyl, —$C_{1-6}$alkenyl, —$C_{1-6}$alkynyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^1$, $R^2$, and $R^3$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^4$ is —$C_{1-6}$alkyl, —$C_{3-7}$cycloalkyl, heteroaryl, or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

A is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^9$CO—$C_{0-2}$alkyl-, —$C_{0-2}$alkyl-$NR^9SO_2$—$C_{0-2}$alkyl- or -hetero$C_{0-4}$alkyl;

Y is phenyl optionally substituted with 1-5 independent halogen, —CN, $NO_2$, —$C_{1-6}$alkyl, —$C_{1-6}$alkenyl, —$C_{1-6}$alkynyl, —$OR^5$, —$NR^5R^6$, —C(=$NR^5$)$NR^6R^7$, —N(=$NR^5$)$NR^6R^7$, —$NR^5COR^6$, —$NR^5CO_2R^6$, —$NR^5SO_2R^8$, —$NR^5CONR^6R^7$, —$SR^8$, —$SOR^8$, —$SO_2R^8$, —$SO_2NR^5R^6$, —$COR^5$, —$CO_2R^5$, —$CONR^5R^6$, —C(=$NR^5$)$R^6$, or —C(=$NOR^5$)$R^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —C, $C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^5$, $R^6$, and $R^7$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^8$ is —$C_{1-6}$alkyl, $C_{3-7}$cycloalkyl, heteroaryl, or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

B is —$C_{0-4}$alkyl, —$C_{0-2}$alkyl-SO—$C_{0-2}$yl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^{10}$CO—$C_{0-2}$alkyl-, —$C_{0-2}$alkyl-$NR^{10}SO_2$—$C_{0-2}$alkyl- or -hetero$C_{0-4}$alkyl;

$R^9$ and $R^{10}$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^{11}$, $R^{12}$ and $R^{13}$ is each independently halogen, —$C_{0-6}$alkyl, —$C_{0-6}$alkoxyl, =O, =N($C_{0-4}$alkyl), or —N($C_{0-4}$alkyl)($C_{0-4}$alkyl), wherein optionally two of $R^{11}$, $R^{12}$ and $R^{13}$ are combined to form a cycloalkyl, heterocycloalkyl, aryl or heteroaryl ring fused to the pyrrole moiety; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

any N may be an N-oxide; and wherein any of the alkyl optionally is substituted with 1-9 independent halogens.

In a second aspect, the compound of this invention is represented by Formula (I) or a pharmaceutically acceptable salt thereof, wherein X is aryl or heteroaryl optionally substituted with 1-7 independent halogen, —CN, $NO_2$, —$C_{1-6}$alkyl, —$C_{1-6}$alkenyl, —$C_6$alkynyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —($C_{3-7}$ cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) groups;

R$^1$, R$^2$, and R$^3$ each independently is —C$_{0-6}$alkyl, —C$_{3-7}$cycloalkyl, heteroaryl, or aryl; any of which is optionally substituted with 1-5 independent halogen, —CN, —C$_{1-6}$alkyl, —O(C$_{0-6}$alkyl), —O(C$_{3-7}$cycloalkyl), —O(aryl), —(heteroaryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

R$^4$ is —C$_{1-6}$alkyl, —C$_{3-7}$cycloalkyl, heteroaryl, or aryl; optionally substituted with 1-5 independent halogen, —CN, —C$_{1-6}$alkyl, —O(C$_{0-6}$alkyl), —(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

A is —C$_{0-4}$alkyl, —C$_{0-2}$alkyl-SO—C$_{0-2}$alkyl-, —C$_{0-2}$alkyl-SO$_2$—C$_{0-2}$alkyl-, —C$_{0-2}$alkyl-CO—C$_{0-2}$alkyl-, C$_{0-2}$alkyl-NR$^9$CO—C$_{0-2}$alkyl-, —C$_{0-2}$alkyl-R$^9$SO$_2$—C$_{0-2}$alkyl- or -heteroC$_{0-4}$alkyl;

Y is 2-pyridyl optionally substituted with 1-4 independent halogen, —CN, NO$_2$, —C$_{1-6}$alkyl, —C$_{1-6}$alkenyl, —C$_{1-6}$alkynyl, —OR$^5$, —NR$^5$R$^6$, —C(=NR$^5$)NR$^6$R$^7$, —N(=NR$^5$)NR$^6$R$^7$, —NR$^5$COR$^6$, —NR$^5$CO$_2$R$^6$, —NR$^5$SO$_2$R$^8$, —NR$^5$CONR$^6$R$^7$, —SR$^8$, —SOR$^8$, —SO$_2$R$^8$, —SO$_2$NR$^5$R$^6$, —COR$^5$, —CO$_2$R$^5$, —CONR$^5$R$^6$, —C(=NR$^5$)R$^6$, or —C(=NOR$^5$)R$^6$ substituents, wherein optionally two substituents are combined to form a cycloalkyl or heterocycloalkyl ring fused to Y; wherein the —C$_{1-6}$alkyl substituent, cycloalkyl ring, or heterocycloalkyl ring each optionally is further substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) groups;

R$^5$, R$^6$, and R$^7$ each independently is —C$_{0-6}$alkyl, —C$_{3-7}$cycloalkyl, heteroaryl, or aryl; any of which is optionally substituted with 1-5 independent halogen, —CN, —C$_{1-16}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

R$^8$ is —C$_{1-6}$alkyl, —C$_{3-7}$cycloalkyl, heteroaryl, or aryl; optionally substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

B is —O$_4$alkyl, —C$_{0-2}$alkyl-SO—C$_{0-2}$alkyl-, —C$_{0-2}$alkyl-SO$_2$—C$_{0-2}$alkyl-, —C$_{0-2}$alkyl-CO—C$_{0-2}$alkyl-, —C$_{0-2}$alkyl-NR$^{10}$CO—C$_{0-2}$alkyl-, —C$_{0-2}$alkyl-NR$^{11}$SO$_2$—C$_{0-2}$alkyl- or -heteroC$_{0-4}$alkyl;

R$^9$ and R$^{10}$ each independently is —C$_{0-6}$alkyl, —C$_{3-7}$cycloalkyl, heteroaryl, or aryl; any of which is optionally substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

R$^{11}$, R$^{12}$ and R$^{13}$ is each independently halogen, —C$_{0-6}$alkyl, —C$_{0-6}$alkoxyl, =O, =N(C$_{0-4}$alkyl), or —N(C$_{0-4}$alkyl)(C$_{0-4}$alkyl), wherein optionally two of R$^{11}$, R$^{12}$ and R$^{13}$ are combined to form a cycloalkyl, heterocycloalkyl, aryl or heteroaryl ring fused to the pyrrole moiety; wherein the —C$_{1-6}$alkyl substituent, cycloalkyl ring, or heterocycloalkyl ring each optionally is further substituted with 1-5 independent halogen, —CN, —C$_{1-6}$alkyl, —O(CO$_6$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) groups;

any N may be an N-oxide; and wherein any of the alkyl optionally is substituted with 1-9 independent halogens.

In an embodiment of this second aspect, the compound of this invention is represented by Formula (I) or a pharmaceutically acceptable salt thereof, wherein X is pyridyl optionally substituted with 1-4 independent halogen, —CN, NO$_2$, —C$_{1-6}$alkyl, —C$_{1-6}$alkenyl, —C$_{1-6}$alkynyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$, —SR$^4$, —SOR$^4$, SO$_2$R$^4$, —SO$_2$NR$^1$R$^2$, —COR$^1$, —CO$_2$R$^1$, —CONR$^1$R$^2$, —C(=NR$^1$)R$^2$, or —C(=NOR$^1$)R$^2$ substituents, wherein optionally two substituents are combined to form a cycloalkyl or heterocycloalkyl ring fused to X; wherein the —C$_{1-6}$alkyl substituent, cycloalkyl ring, or heterocycloalkyl ring each optionally is further substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) groups;

R$^1$, R$^2$, and R$^3$ each independently is —C$_{0-6}$alkyl, —C$_{3-7}$cycloalkyl, heteroaryl, or aryl; any of which is optionally substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

R$^4$ is —C$_{1-6}$alkyl, —C$_{3-7}$cycloalkyl, heteroaryl, or aryl; optionally substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

A is —C$_{0-4}$alkyl, —C$_{0-2}$alkyl-SO—C$_{0-2}$alkyl-, C$_{0-2}$alkyl-SO$_2$—C$_{0-2}$alkyl-, —C$_{0-2}$alkyl-CO—C$_{0-2}$alkyl-, —C$_{0-2}$alkyl-NR$^9$CO—C$_{0-2}$alkyl-, —C$_{0-2}$alkyl-NR$^9$SO$_2$—C$_{0-2}$alkyl- or -heteroC$_{0-4}$alkyl;

Y is 2-pyridyl optionally substituted with 14 independent halogen, —CN, NO$_2$, —C$_{1-6}$alkyl, —C$_{1-6}$alkenyl, —C$_{1-6}$alkynyl, —OR$^5$, —NR$^5$R$^6$, —C(=NR$^5$)NR$^6$R$^7$, —N(=NR$^5$)NR$^6$R$^7$, —NR$^5$COR$^6$, —NR$^5$CO$_2$R$^6$, —NR$^5$SO$_2$R$^8$, —NR$^5$CONR$^6$R$^7$, —SR$^8$, —SOR$^8$, —SO$_2$R$^8$, —O$_2$NR$^5$R$^6$, —COR$^5$, —CO$_2$R$^5$, —CONR$^5$R$^6$, —C(=NR$^5$)R$^6$, or —C(=NOR$^5$)R$^6$ substituents, wherein optionally two substituents are combined to form a cycloalkyl or heterocycloalkyl ring fused to Y; wherein the —C$_{1-6}$alkyl substituent, cycloalkyl ring, or heterocycloalkyl ring each optionally is further substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) groups;

R$^5$, R$^6$, and R$^7$ each independently is —C$_{0-6}$alkyl, —C$_{3-7}$cycloalkyl, heteroaryl, or aryl; any of which is optionally substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

R$^8$ is —C$_{1-6}$alkyl, —C$_{3-7}$cycloalkyl, heteroaryl, or aryl; optionally substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

B is —C$_{0-4}$alkyl, —C$_{0-2}$alkyl-SO—C$_{0-2}$alkyl-, —C$_{0-2}$alkyl-SO$_2$—C$_{0-2}$alkyl-, —C$_{0-2}$alkyl-CO—C$_{0-2}$alkyl-, —C$_{0-2}$alkyl-NR$^{10}$CO—C$_{0-2}$alkyl-, —C$_{0-2}$alkyl-NR$^{10}$SO$_2$—C$_{0-2}$alkyl- or -heteroC$_{0-4}$alkyl;

$R^9$ and $R^{10}$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^{11}$, $R^{12}$ and $R^{13}$ is each independently halogen, —$C_{0-6}$alkyl, —$C_{0-6}$alkoxyl, =O, =N($C_{0-4}$alkyl), or —N($C_{0-4}$alkyl)($C_{0-4}$alkyl), wherein optionally two of $R^{11}$, $R^{12}$ and $R^{13}$ are combined to form a cycloalkyl, heterocycloalkyl, aryl or heteroaryl ring fused to the pyrrole moiety; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

any N may be an N-oxide; and wherein any of the alkyl optionally is substituted with 1-9 independent halogens.

In a third aspect the compound of this invention is represented by Formula (I) or a pharmaceutically acceptable salt thereof, wherein X is phenyl optionally substituted with 1-5 independent halogen, —CN, $NO_2$, —$C_{1-6}$alkyl, —$C_{1-6}$alkenyl, —$C_{1-6}$alkynyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^1$, $R^2$, and $R^3$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^4$ is —$C_{1-6}$alkyl, —$C_{3-7}$cycloalkyl, heteroaryl, or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

A is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^9$CO—$C_{0-2}$alkyl-, —$C_{0-2}$alkyl-$NR^9SO_2$—$C_{0-2}$alkyl- or -hetero$C_{0-4}$alkyl;

Y is aryl or heteroaryl optionally substituted with 1-7 independent halogen, —CN, $NO_2$, —$C_{1-6}$alkyl, —$C_{1-6}$alkenyl, —$C_{1-6}$alkynyl, —$OR^5$, —$NR^5R^6$, —C(=$NR^5$)$NR^6R^7$, —N(=$NR^5$)$NR^6R^7$, —$NR^5COR^6$, —$NR^5CO_2R^6$, —$NR^5SO_2R^8$, —$NR^5CONR^6R^7$, —$SR^8$, —$SOR^8$, —$SO_2R^8$, —$SO_2NR^5R^6$, —$COR^5$, —$CO_2R^5$, —$CONR^5R^6$, —C(=$NR^5$)$R^6$, or —C(=$NOR^5$)$R^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —C, —$C_{1-16}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^5$, $R^6$, and $R^7$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^8$ is —$C_{1-6}$alkyl, —$C_{3-7}$cycloalkyl, heteroaryl, or aryl; optionally substituted with 1-5 independent halogen, —CN, —$C_{1-16}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

B is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^{10}$CO—$C_{0-2}$alkyl-, —$C_{0-2}$alkyl-$NR^{10}SO_2$—$C_{0-2}$alkyl- or -hetero$C_{0-4}$alkyl;

$R^9$ and $R^{10}$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^{11}$, $R^{12}$ and $R^{13}$ is each independently halogen, —$C_{0-6}$alkyl, —$C_{0-6}$alkoxyl, =O, =N($C_{0-4}$alkyl), or —N($C_{0-4}$alkyl)($C_{0-4}$alkyl), wherein optionally two of $R^{11}$, $R^{12}$ and $R^{13}$ are combined to form a cycloalkyl, heterocycloalkyl, aryl or heteroaryl ring fused to the pyrrole moiety; wherein the —$C_{1-6}$alkyl substituent, cycloalkyl ring, or heterocycloalkyl ring each optionally is further substituted with 1-5 independent halogen, —CN, $C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

any N may be an N-oxide; and wherein any of the alkyl optionally is substituted with 1-9 independent halogens.

In an embodiment of this third aspect, the compound of this invention is represented by Formula (I) or a pharmaceutically acceptable salt thereof, wherein X is phenyl optionally substituted with 1-5 independent halogen, —CN, $NO_2$, —$C_{1-6}$alkyl, —$C_{1-6}$alkenyl, —$C_{1-6}$alkyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl-, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^1$, $R^2$, and $R^3$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^4$ is —$C_{1-6}$alkyl, —$C_{3-7}$cycloalkyl, heteroaryl, or aryl; optionally substituted with 1-5 independent halogen, —C, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

A is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^9$CO—$C_{0-2}$alkyl-, —$C_{0-2}$alkyl-$NR^9SO_2$—$C_{0-2}$alkyl- or -hetero$C_{0-4}$alkyl;

Y is 2-pyridyl optionally substituted with 1-4 independent halogen, —CN, $NO_2$, —$C_{1-6}$alkyl, —$C_{1-6}$alkenyl, —$C_{1-6}$alkynyl, —$OR^5$, —$NR^5R^6$, —C(=$NR^5$)$NR^6R^7$, —N(=$NR^5$)$NR^6R^7$, —$NR^5COR^6$, —$NR^5CO_2R^6$, —$NR^5SO_2R^8$, —$NR^5CONR^6R^7$, —$SR^8$, —$SOR^8$, —$SO_2R^8$, —$SO_2NR^5R^6$, —$COR^5$, —$CO_2R^5$, —$CONR^5R^6$, —C(=$NR^5$)$R^6$, or —C(=$NOR^5$)$R^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^5$, $R^6$, and $R^7$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^8$ is —$C_{1-6}$alkyl, —$C_{3-7}$cycloalkyl, heteroaryl, or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

B is —$C_{0-4}$alkyl, —$C_{0-2}$alky-SO—$C_{0-2}$alkyl-, —$C_{0-2}$alkyl-$SO_2$—$C_{0-2}$alkyl-, —CO$_2$alkyl-CO—$C_{0-2}$alkyl-, —$C_{0-2}$alkyl-$NR^{10}$CO—$C_{0-2}$alkyl-, —$C_{0-2}$alkyl-$NR^{10}SO_2$—$C_{0-2}$alkyl- or -hetero$C_{0-4}$alkyl;

$R^9$ and $R^{10}$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^{11}$, $R^{12}$ and $R^{13}$ is each independently halogen, —$C_{0-6}$alkyl, —$C_{0-6}$alkoxyl, =O, =N($C_{0-4}$alkyl), or —N($C_{0-4}$alkyl)($C_{0-4}$alkyl), wherein optionally two of $R^{11}$, $R^{12}$ and $R^{13}$ are combined to form a cycloalkyl, heterocycloalkyl, aryl or heteroaryl ring fused to the pyrrole moiety; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

any N may be an N-oxide; and wherein any of the alkyl optionally is substituted with 1-9 independent halogens.

In a fourth aspect, the compound of this invention is represented by Formula (I) or a pharmaceutically acceptable salt thereof, wherein X is aryl or heteroaryl optionally substituted with 1-7 independent halogen, —CN, $NO_2$, —$C_{1-6}$alkyl, —$C_{1-6}$alkenyl, —$C_{1-6}$alkynyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^1$, $R^2$, and $R^3$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^4$ is —$C_{1-6}$alkyl, —$C_{3-7}$cycloalkyl, heteroaryl, or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

A is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^9$CO—$C_{0-2}$alkyl-, —$C_{0-2}$alkyl-$NR^9SO_2$—$C_{0-2}$alkyl- or -hetero$C_{0-4}$alkyl;

Y is 1,3-thiazol-2-yl optionally substituted with 1-2 independent halogen, —CN, $NO_2$, —$C_{1-6}$alkyl, —$C_{1-6}$alkenyl, —$C_{1-6}$alkyl, —$OR^5$, —$NR^5R^6$, —C(=$NR^5$)$NR^6R^7$, —N(=$NR^5$)$NR^6R^7$, —$NR^5COR^6$, —$NR^5CO_2R^6$, —$NR^5SO_2R^8$, —$NR^5CONR^6R^7$, —$R^8$, —$SOR^8$, —$SO_2R^8$, —$SO_2NR^5R^6$, —$COR^5$, —$CO_2R^5$, —$CONR^5R^6$, —C(=$NR^5$)$R^6$, or —C(=$NOR^5$)$R^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^5$, $R^6$, and $R^7$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^8$ is —$C_{1-6}$alkyl, —$C_{3-7}$cycloalkyl, heteroaryl, or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

B is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^{10}$CO—$C_{0-2}$alkyl-, —$C_{0-2}$alkyl-$NR^{10}SO^2$—$C_{0-2}$alkyl- or -hetero$C_{0-4}$alkyl;

$R^9$ and $R^{10}$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^{11}$, $R^{12}$ and $R^{13}$ is each independently halogen, —$C_{0-6}$alkyl, —$C_{0-6}$alkoxyl, =O, =N($C_{0-4}$alkyl), or —N($C_{0-4}$alkyl)($C_{0-4}$alkyl), wherein optionally two of $R^{11}$, $R^{12}$ and $R^{13}$ are combined to form a cycloalkyl, heterocycloalkyl, aryl or heteroaryl ring fused to the pyrrole moiety; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

any N may be an N-oxide; and wherein any of the alkyl optionally is substituted with 1-9 independent halogens.

In an embodiment of this fourth aspect, the compound of this invention is represented by Formula (I) or a pharmaceutically acceptable salt thereof, wherein X is phenyl optionally substituted with 1-5 independent halogen, —CN, NO$_2$, —$C_{1-6}$alkyl, —$C_{1-6}$alkenyl, —$C_{1-6}$alkynyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(=NR$^1$)R$^2$, or —C(=NOR$^1$)R$^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

R$^1$, R$^2$, and R$^3$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

R$^4$ is —$C_{1-6}$alkyl, —$C_{3-7}$cycloalkyl, heteroaryl, or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

A is —$C_{0-4}$alkyl, —$C_{0-2}$alkyl-SO—$C_{0-2}$alkyl-, —$C_{0-2}$alkyl-SO$_2$—$C_{0-2}$alkyl-, —$C_{0-2}$alkyl-CO—$C_{0-2}$alkyl-, —$C_{0-2}$alkyl-NR$^9$CO—$C_{0-2}$alkyl-, —$C_{0-2}$alkyl-NR$^9$SO$_2$—$C_{0-2}$alkyl- or -hetero$C_{0-4}$alkyl;

Y is 1,3-thiazol-2-yl optionally substituted with 1-2 independent halogen, —CN, NO$_2$, —$C_{1-6}$alkyl, —$C_{1-6}$alkenyl, —$C_{1-6}$alkynyl, —OR$^5$, —NR$^5$R$^6$, —C(=NR$^5$)NR$^6$R$^7$, —N(=NR$^5$)NR$^6$R$^7$, —NR$^5$COR$^6$, —NR$^5$CO$_2$R$^6$, —NR$^5$SO$_2$R$^8$, —NR$^5$CONR$^6$R$^7$, —SR$^8$, —SOR$^8$, —SO$_2$R$^8$, —SO$_2$NR$^5$R$^6$, —COR$^5$, —CO$_2$R$^5$, —CONR$^5$R$^6$, —C(=NR$^5$)R$^6$, or —C(=NOR$^5$)R$^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-16}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

R$^5$, R$^6$, and R$^7$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

R$^8$ is —$C_{1-6}$alkyl, —$C_{3-7}$cycloalkyl, heteroaryl, or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

B is —$C_{0-4}$alkyl, —$C_{0-2}$alkyl-SO—$C_{0-2}$alkyl-, —$C_{0-2}$alkyl-SO$_2$—$C_{0-2}$alkyl-, —$C_{0-2}$alkyl-CO—$C_{0-2}$alkyl-, —$C_{0-2}$alkyl-NR$^{10}$CO—$C_{0-2}$alkyl-, —$C_{0-2}$alkyl-NR$^{10}$SO$_2$—$C_{0-2}$alkyl- or -hetero$C_{0-4}$alkyl;

R$^9$ and R$^{10}$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

R$^{11}$, R$^{12}$ and R$^{13}$ is each independently halogen, —$C_{0-6}$alkyl, —$C_{0-6}$alkoxyl, =O, =N($C_{0-4}$alkyl), or —N($C_{0-4}$alkyl)($C_{0-4}$alkyl), wherein optionally two of R$^{11}$, R$^{12}$ and R$^{13}$ are combined to form a cycloalkyl, heterocycloalkyl, aryl or heteroaryl ring fused to the pyrrole moiety; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

any N may be an N-oxide; and wherein any of the alkyl optionally is substituted with 1-9 independent halogens.

In a fifth aspect, the compound of this invention is represented by Formula (I) or a pharmaceutically acceptable salt thereof, wherein X is aryl or heteroaryl optionally substituted with 1-7 independent halogen, —CN, NO$_2$, —$C_{1-6}$alkyl, —$C_{1-6}$alkenyl, —$C_{1-6}$alkyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(=NR$^1$)R$^2$, or —C(=NOR$^1$)R$^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(eteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

R$^1$, R$^2$, and R$^3$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

R$^4$ is —$C_{1-6}$alkyl, —$C_{3-7}$cycloalkyl, heteroaryl, or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

A is —$C_{0-4}$alkyl, —$C_{0-2}$alkyl-SO—$C_{0-2}$alkyl-, —$C_{0-2}$alkyl-SO$_2$—$C_{0-2}$alkyl-, —$C_{0-2}$alkyl-CO—$C_{0-2}$alkyl-, —$C_{0-2}$alkyl-NR$^9$CO—$C_{0-2}$alkyl-, —$C_{0-2}$alkyl-NR$^9$SO$_2$—$C_{0-2}$alkyl- or -hetero$C_{0-4}$alkyl;

Y is pyrazolyl optionally substituted with 1-3 independent halogen, —CN, NO$_2$, —$C_{1-6}$alkyl, —$C_{1-6}$alkenyl, —$C_{1-6}$alkynyl, —OR$^5$, —NR$^5$R$^6$, —C(=NR$^5$)NR$^6$R$^7$, —N(=NR$^5$)NR$^6$R$^7$, —NR$^5$COR$^6$, —NR$^5$CO$_2$R$^6$, —NR$^5$SO$_2$R$^8$, —NR$^5$CONR$^6$R$^7$, —SR$^8$, —SOR$^8$, —SO$_2$R$^8$, —SO$_2$NR$^5$R$^6$, —COR$^5$, —CO$_2$R$^5$, —CONR$^5$R$^6$, —C(=NR$^5$)R$^6$, or —C(=NOR$^5$)R$^6$ substituents, wherein optionally two substituents are combined to form a cycloalkyl or heterocycloalkyl ring fused to Y; wherein the —C$_{1-6}$alkyl substituent, cycloalkyl ring, or heterocycloalkyl ring each optionally is further substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) groups;

R$^5$, R$^6$, and R$^7$ each independently is —C$_{0-6}$alkyl, —C$_{3-7}$cycloalkyl, heteroaryl, or aryl; any of which is optionally substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

R$^8$ is —C$_{1-6}$alkyl, —C$_{3-7}$cycloalkyl, heteroaryl, or aryl; optionally substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

B is —C$_{0-4}$alkyl, —C$_{0-2}$alkyl-SO—C$_{0-2}$alkyl-, —C$_{0-2}$alkyl-SO$_2$—C$_{0-2}$alkyl-, —C$_{0-2}$alkyl-CO—C$_{0-2}$alkyl-, —C$_{0-2}$alkyl-NR$^{10}$CO—C$_{0-2}$alkyl-, —C$_{0-2}$alkyl-NR$^{10}$SO$_2$—C$_{0-2}$alkyl- or -heteroC$_{0-4}$alkyl;

R$^9$ and R$^{10}$ each independently is —C$_{0-6}$alkyl, —C$_{3-7}$cycloalkyl, heteroaryl, or aryl; any of which is optionally substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

R$^{11}$, R$^{12}$ and R$^{13}$ is each independently halogen, —C$_{0-6}$alkyl, —C$_{0-6}$alkoxyl, =O, =N(C$_{0-4}$alkyl), or —N(C$_{0-4}$alkyl)(C$_{0-4}$alkyl), wherein optionally two of R$^{11}$, R$^{12}$ and R$^{13}$ are combined to form a cycloalkyl, heterocycloalkyl, aryl or heteroaryl ring fused to the pyrrole moiety; wherein the —C$_{1-6}$alkyl substituent, cycloalkyl ring, or heterocycloalkyl ring each optionally is further substituted with 1-5 independent halogen, —CN, —C$_{1-6}$alkyl, —O(C$_{0-6}$alkyl), —O(C$_{3-7}$cycloakyl), —O(aryl), —O(heteroaryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) groups;

any N may be an N-oxide; and wherein any of the alkyl optionally is substituted with 1-9 independent halogens.

In an embodiment of this fifth aspect, the compound of this invention is represented by Formula (I) or a pharmaceutically acceptable salt thereof, wherein X is phenyl optionally substituted with 1-5 independent halogen, —CN, NO$_2$, —C$_{1-6}$alkyl, —C$_{1-6}$alkenyl, —C$_6$alkynyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(=NR$^1$)R$^2$, or —C(=NOR$^1$)R$^2$ substituents, wherein optionally two substituents are combined to form a cycloalkyl or heterocycloalkyl ring fused to X; wherein the —C$_{1-6}$alkyl substituent, cycloalkyl ring, or heterocycloalkyl ring each optionally is further substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) groups;

R$^1$, R$^2$, and R$^3$ each independently is —C$_{0-6}$alkyl, —C$_{3-7}$cycloalkyl, heteroaryl, or aryl; any of which is optionally substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(aryl) substituents;

R$^4$ is —C$_{1-6}$alkyl, —C$_{3-7}$cycloalkyl, heteroaryl, or aryl; optionally substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

A is —C$_{0-4}$alkyl, —C$_{0-2}$alkyl-SO—C$_{0-2}$alkyl-, —C$_{0-2}$alkyl-SO$_2$—C$_{0-2}$alkyl-, —C$_{0-2}$alkyl-CO—C$_{0-2}$alkyl-, —C$_{0-2}$alkyl-NR$^9$CO—C$_{0-2}$alkyl-, —C$_{0-2}$alkyl-NR$^9$SO$_2$—C$_{0-2}$alkyl- or -heteroC$_{0-4}$alkyl;

Y is pyrazolyl optionally substituted with 1-2 independent halogen, —CN, NO$_2$, —C$_{1-6}$alkyl, —C$_{1-6}$alkenyl, —C$_{1-6}$alkyl, —OR$^5$, —NR$^5$R$^6$, —C(=NR$^5$)NR$^6$R$^7$, —N(=NR$^5$)NR$^6$R$^7$, —NR$^5$COR$^6$, —NR$^5$CO$_2$R$^6$, —NR$^5$SO$_2$R$^8$, —NR$^5$CONR$^6$R$^7$, —SR$^8$, —SOR$^8$, —SO$_2$R$^8$, —SO$_2$NR$^5$R$^6$, —COR$^5$, —CO$_2$R$^5$, —CONR$^5$R$^6$, —C(=NR$^5$)R$^6$, or —C(=NOR$^5$)R$^6$ substituents, wherein optionally two substituents are combined to form a cycloalkyl or heterocycloalkyl ring fused to Y; wherein the —C$_{1-6}$alkyl substituent, cycloalkyl ring, or heterocycloalkyl ring each optionally is further substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) groups;

R$^5$, R$^6$, and R$^7$ each independently is —C$_{0-6}$alkyl, —C$_{3-7}$cycloalkyl, heteroaryl, or aryl; any of which is optionally substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

R$^8$ is —C$_{1-6}$alkyl, —C$_{3-7}$cycloalkyl, heteroaryl, or aryl; optionally substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

B is —C$_{0-4}$alkyl, —C$_{0-2}$alkyl-SO—C$_{0-2}$alkyl-, —CO$_2$alkyl-SO$_2$—C$_{0-2}$alkyl-, —C$_{0-2}$alkyl-CO—C$_{0-2}$alkyl-, —C$_{0-2}$alkyl-NR$^{10}$CO—C$_{0-2}$alkyl-, —C$_2$alkyl-NR$^{10}$SO$_2$ C$_{0-2}$alkyl- or -heteroC$_{0-4}$alkyl;

R$^9$ and R$^{10}$ each independently is —C$_{0-6}$alkyl, —C$_{3-7}$cycloalkyl, heteroaryl, or aryl; any of which is optionally substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

R$^{11}$, R$^{12}$ and R$^{13}$ is each independently halogen, —C$_{0-6}$alkyl, C$_{0-6}$alkoxyl, =O, =N(C$_{0-4}$alkyl), or —N(C$_{0-4}$alkyl)(C$_{0-4}$alkyl), wherein optionally two of R$^{11}$, R$^{12}$ and R$^{13}$ are combined to form a cycloalkyl, heterocycloalkyl, aryl or heteroaryl ring fused to the pyrrole moiety; wherein the —C$_{1-6}$alkyl substituent, cycloalkyl ring, or heterocycloalkyl ring each optionally is further substituted with 1-5 independent halogen, —C, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) groups;

any N may be an N-oxide; and wherein any of the alkyl optionally is substituted with 1-9 independent halogens.

Thus, the compound of this invention is represented by Formula (I) or a pharmaceutically acceptable salt thereof, wherein X is 2-pyridyl optionally substituted with 1-4 independent halogen, —CN, NO$_2$, —C$_{1-6}$alkyl, —C$_{1-6}$alkenyl, —C$_{1-6}$alkynyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(=NR$^1$)R$^2$, or —C(=NOR$^1$)R$^2$ substituents, wherein optionally two substituents are combined to form a cycloalkyl or heterocycloalkyl ring fused to X; wherein the —C$_{1-6}$alkyl substituent, cycloalkyl ring, or heterocycloalkyl ring each optionally is further substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) groups.

Further, the compound of this invention is represented by Formula (I) or a pharmaceutically acceptable salt thereof, wherein X is 2-pyridyl optionally substituted with 1-4 independent halogen, —CN, NO$_2$, —C$_{1-6}$alkyl, —C$_{1-6}$alkenyl, —C$_{1-6}$alkynyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(=NR$^1$)R$^2$, or —C(=NOR$^1$)R$^2$ substituents, wherein optionally two substituents are combined to form a cycloalkyl or heterocycloalkyl ring fused to X; wherein the —C$_{1-6}$alkyl substituent, cycloalkyl ring, or heterocycloalkyl ring each optionally is further substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) groups; and Y is phenyl optionally substituted with 1-5 independent halogen, —CN, NO$_2$, —C$_{1-6}$alkyl, —C$_{1-6}$alkenyl, —C$_{1-6}$alkynyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(=NR$^1$)R$^2$, or —C(=NOR$^1$)R$^2$ substituents, wherein optionally two substituents are combined to form a cycloalkyl or heterocycloalkyl ring fused to Y; wherein the —C$_{1-6}$alkyl substituent, cycloalkyl ring, or heterocycloalkyl ring each optionally is further substituted with 1-5 independent halogen, —CN, —C$_{1-16}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) groups.

Still further, the compound of this invention is represented by Formula (I) or a pharmaceutically acceptable salt thereof, wherein X is aryl or heteroaryl optionally substituted with 1-7 independent halogen, —CN, NO$_2$, —C$_{1-6}$alkyl, —C$_{1-6}$alkenyl, —C$_{1-6}$alkynyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$—SO$_2$NR$^1$R$^2$, —COR$^1$, —CO$_2$R$^1$, —CONR$^1$R$^2$, —C(=NR$^1$)R$^2$, or —C(=NOR$^1$)R$^2$ substituents, wherein optionally two substituents are combined to form a cycloalkyl or heterocycloalkyl ring fused to X; wherein the —C$_{1-6}$alkyl substituent, cycloalkyl ring, or heterocycloalkyl ring each optionally is further substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) groups; and Y is 2-pyridyl optionally substituted with 1-4 independent halogen, —CN, NO$_2$, —C$_{1-6}$alkyl, —C$_{1-6}$alkenyl, —C$_{1-6}$alkynyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(=NR$^1$)R$^2$, or —C(=NOR$^1$)R$^2$ substituents, wherein optionally two substituents are combined to form a cycloalkyl or heterocycloalkyl ring fused to Y; wherein the —C$_{1-6}$alkyl substituent, cycloalkyl ring, or heterocycloalkyl ring each optionally is further substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) groups.

Even further, the compound of this invention is represented by Formula (I) or a pharmaceutically acceptable salt thereof, wherein X is pyridyl optionally substituted with 1-4 independent halogen, —CN, NO$_2$, —C$_{1-6}$alkyl, —C$_{1-6}$alkenyl, —C$_{1-6}$alkynyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(=NR$^1$)R$^2$, or —C(=NOR$^1$)R$^2$ substituents, wherein optionally two substituents are combined to form a cycloalkyl or heterocycloalkyl ring fused to X; wherein the —C$_{1-6}$alkyl substituent, cycloalkyl ring, or heterocycloalkyl ring each optionally is further substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) groups; and Y is 2-pyridyl optionally substituted with 14 independent halogen, —CN, NO$_2$, —C$_{1-6}$alkyl, —C$_{1-6}$alkenyl, —C$_{1-6}$alkynyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(—NR$^1$)R$^2$, or —C(=NOR$^1$)R$^2$ substituents, wherein optionally two substituents are combined to form a cycloalkyl or heterocycloalkyl ring fused to Y; wherein the —C$_{1-6}$alkyl substituent, cycloalkyl ring, or heterocycloalkyl ring each optionally is further substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) groups.

Still further, the compound of this invention is represented by Formula (I) or a pharmaceutically acceptable salt thereof, wherein X is phenyl optionally substituted with 1-5 independent halogen, —CN, NO$_2$, —C$_{1-6}$alkyl, —C$_{1-6}$alkenyl, —C$_{1-6}$alkynyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(=NR$^1$R$^2$, or —C(=NOR$^1$)R$^2$ substituents, wherein optionally two substituents are combined to form a cycloalkyl or heterocycloalkyl ring fused to X; wherein the —C$_{1-6}$alkyl substituent, cycloalkyl ring, or heterocycloalkyl ring each optionally is further substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) groups.

Even further, the compound of this invention is represented by Formula (I) or a pharmaceutically acceptable salt thereof, wherein X is phenyl optionally substituted with 1-5 independent halogen, —CN, $NO_2$, —$C_{1-6}$alkyl, —$C_{1-6}$alkenyl, —$C_{1-6}$alkynyl, —$OR^1$, —$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —$C(=NR^1)R^2$, or —$C(=NOR^1)R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —$O(C_{0-6}$alkyl), —$O(C_{3-7}$cycloalkyl), —O(aryl), —O(heteroaryl), —$N(C_{0-6}$alkyl)($C_{0-6}$alkyl), —$N(C_{0-6}$alkyl)($C_{3-7}$cycloalkyl), or —$N(C_{0-6}$alkyl)(aryl) groups; and Y is 2-pyridyl optionally substituted with 1-4 independent halogen, —CN, $NO_2$, —$C_{1-6}$alkyl, —$C_{1-6}$alkenyl, —$C_{1-6}$alkynyl, —$OR^1$, —$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —$C(=NR^1)R^2$, or —$C(=NOR^1)R^2$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —$O(C_{0-6}$alkyl), —$O(C_{3-7}$cycloalkyl), —O(aryl), —O(heteroaryl), —$N(C_{0-6}$alkyl)($C_{0-6}$alkyl), —$N(C_{0-6}$alkyl)($C_{3-7}$cycloalkyl), or —$N(C_{0-6}$alkyl)(aryl) groups.

And, the compound of this invention is represented by Formula (I) or a pharmaceutically acceptable salt thereof, wherein Y is 1,3-thiazol-2-yl optionally substituted with 1-2 independent halogen, —CN, $NO_2$, —$C_{1-6}$alkyl, —$C_{1-6}$alkenyl, —$C_{1-6}$alkynyl, —$OR^1$, —$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —$C(=NR^1)R^2$, or —$C(=NOR^1)R^2$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —$O(C_{0-6}$alkyl), —$O(C_{3-7}$cycloalkyl), —O(aryl), —O(eteroaryl), —$N(C_{0-6}$alkyl)($C_{0-6}$alkyl), —$N(C_{0-6}$alkyl)($C_{3-7}$cycloalkyl), or —$N(C_{0-6}$alkyl)(aryl) groups.

Further, the compound of this invention is represented by Formula (I) or a pharmaceutically acceptable salt thereof, wherein Y is 1,3-thiazol-2-yl optionally substituted with 1-2 independent halogen, —CN, $NO_2$, —$C_{1-6}$alkyl, —$C_{1-6}$alkenyl, —$C_{1-6}$alkynyl, —$OR^1$, —$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —$C(=NR^1)R^2$, or —$C(=NOR^1)R^2$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —$O(C_{0-6}$alkyl), —$O(C_{3-7}$cycloalkyl), —O(aryl), —O(heteroaryl), —$N(C_{0-6}$alkyl)($C_{0-6}$alkyl), —$N(C_{0-6}$alkyl)($C_{3-7}$cycloalkyl), or —$N(C_{0-6}$alkyl)(aryl) groups; and X is phenyl optionally substituted with 1-5 independent halogen, —CN, $NO_2$, —$C_{1-6}$alkyl, —$C_{1-6}$alkenyl, —$C_{1-6}$alkynyl, —$OR^1$, —$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —$C(=NR^1)R^2$, or —$C(=NOR^1)R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —$O(C_{0-6}$alkyl), —$O(C_{3-7}$cycloalkyl), —O(aryl), —O(heteroaryl), —$N(C_{0-6}$alkyl)($C_{0-6}$alkyl), —$N(C_{0-6}$alkyl)($C_{3-7}$cycloalkyl), or —$N(C_{0-6}$alkyl)(aryl) groups.

And, the compound of this invention is represented by Formula (I) or a pharmaceutically acceptable salt thereof, wherein Y is pyrazolyl optionally substituted with 1-3 independent halogen, —CN, $NO_2$, —$C_{1-6}$alkyl, —$C_{1-6}$alkenyl, —$C_{1-6}$alkyl, —$OR^1$, —$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, $SO_2R^4$, —$SO_2NR^1R^2$, —$COR^1$, —$CO_2R^1$, —$CONR^1R^2$, —$C(=NR^1)R^2$, or —$C(=NOR^1)R^2$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —$O(C_{0-6}$alkyl), —$O(C_{3-7}$cycloalkyl), —O(aryl), —O(heteroaryl), —$N(C_{0-6}$alkyl)($C_{0-6}$alkyl), —$N(C_{0-6}$alkyl)($C_{3-7}$cycloalkyl), or —$N(C_{0-6}$alkyl)(aryl) groups.

Further, the compound of this invention is represented by Formula (I) or a pharmaceutically acceptable salt thereof, wherein Y is pyrazolyl optionally substituted with 1-3 independent halogen, —CN, $NO_2$, —$C_{1-6}$alkyl, —$C_{1-6}$alkenyl, —$C_{1-6}$alkynyl, —$OR^1$, —$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —$C(=NR^1)R^2$, or —$C(=NOR^1)R^2$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —$O(C_{0-6}$alkyl), —$O(C_{3-7}$cycloalkyl), —O(aryl), —O(heteroaryl), —$N(C_{0-6}$alkyl)($C_{0-6}$alkyl), —$N(C_{0-6}$alkyl)($C_{3-7}$cycloalkyl), or —$N(C_{0-6}$alkyl)(aryl) groups; and X is phenyl optionally substituted with 1-5 independent halogen, —CN, $NO_2$, —$C_{1-6}$alkyl, —$C_{1-6}$alkenyl, —$C_{1-6}$alkyl, —$OR^1$, —$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —$C(=NR^1)R^2$, or —$C(=NOR^1)R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —$O(C_{0-6}$alkyl), —$O(C_{3-7}$ cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups.

As used herein, "alkyl" as well as other groups having the prefix "alk" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains containing at least one unsaturated C—C bond.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, indenyl, fluorenyl, 1,2,3,4-tetrahydronaphalene and the like. Similarly, "cycloalkenyl" means carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, indenyl, and the like.

The term "aryl" means an aromatic substituent which is a single ring or multiple rings fused together. When formed of multiple rings, at least one of the constituent rings is aromatic. The preferred aryl substituents are phenyl and naphthyl groups.

The term "cycloalkyloxy" unless specifically stated otherwise includes a cycloalkyl group connected by a short $C_{1-2}$alkyl length to the oxy connecting atom.

The term "$C_{0-6}$alkyl" includes alkyls containing 6, 5, 4, 3, 2, 1, or no carbon atoms. An alkyl with no carbon atoms is a hydrogen atom substituent when the alkyl is a terminal group and is a direct bond when the alkyl is a bridging group.

The term "hetero" unless specifically stated otherwise includes one or more O, S, or N atoms. For example, heterocycloalkyl and heteroaryl include ring systems that contain one or more O, S, or N atoms in the ring, including mixtures of such atoms. The hetero atoms replace ring carbon atoms. Thus, for example, a heterocyclo$C_5$alkyl is a five-member ring containing from 4 to no carbon atoms. Examples of heteroaryls include pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, benzoxazolyl, isoxazolyl, thiazolyl, benzothiazolyl, isothiazolyl, imidazolyl, benzimidazolyl, oxadiazolyl, thiadiazolyl, triazolyl, and tetrazolyl. Examples of heterocycloalkyls include azetidinyl, pyrrolidinyl, piperidinyl, piperazinyl, morpholinyl, tetrahydrofuranyl, imidazolinyl, pyrolidin-2-one, piperidin-2-one, and thiomorpholinyl.

The term "hetero$C_{0-4}$alkyl" means a heteroalkyl containing 3, 2, 1, or no carbon atoms. However, at least one heteroatom must be present. Thus, as an example, a hetero$C_{0-4}$alkyl having no carbon atoms but one N atom would be a —NH— if a bridging group and a —$NH_2$ if a terminal group. Analogous bridging or terminal groups are clear for an O or S heteroatom.

The term "amine" unless specifically stated otherwise includes primary, secondary and tertiary amines substituted with $C_{0-6}$alkyl.

The term "carbonyl" unless specifically stated otherwise includes a $C_{0-6}$alkyl substituent group when the carbonyl is terminal.

The term "halogen" includes fluorine, chlorine, bromine and iodine atoms.

The term "optionally substituted" is intended to include both substituted and unsubstituted. Thus, for example, optionally substituted aryl could represent a pentafluorophenyl or a phenyl ring. Further, optionally substituted multiple moieties such as, for example, alkylaryl are intended to mean that the aryl and the aryl groups are optionally substituted. If only one of the multiple moieties is optionally substituted then it will be specifically recited such as "an alkylaryl, the aryl optionally substituted with halogen or hydroxyl."

Compounds described herein contain one or more double bonds and may thus give rise to cis/trans isomers as well as other conformational isomers. The present invention includes all such possible isomers as well as mixtures of such isomers.

Compounds described herein can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, and tartaric acids.

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. Such additional therapeutic ingredients include, for example, i) opiate agonists or antagonists, ii) calcium channel antagonists, iii) 5HT receptor agonists or antagonists iv) sodium channel antagonists, v) NMDA receptor agonists or antagonists, vi) COX-2 selective inhibitors, vii) NK1 antagonists, viii) non-steroidal anti-inflammatory drugs ("NSAID"), ix) GABA-A receptor modulators, x) dopamine agonists or antagonists, xi) selective serotonin reuptake inhibitors ("SSRI") and/or selective serotonin and norepinephrine reuptake inhibitors ("SSNRI"), xii) tricyclic antidepressant drugs, xiv) norepinephrine modulators, xv) L-DOPA, xvi) buspirone, xvii) lithium, xviii) valproate, ixx) neurontin (gabapentin), xx) olanzapine, xxi) nicotine agonists or antagonists including nicotine, xxii) muscarinic agonists or antagonists, xxiii) heroin substituting drugs such as methadone, levo-alpha-acetylmethadol, buprenorphine and naltrexone, and xxiv) disulfirm and acamprosate. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

Creams, ointments, jellies, solutions, or suspensions containing the compound of Formula I can be employed for topical use. Mouth washes and gargles are included within the scope of topical use for the purposes of this invention.

Dosage levels from about 0.01 mg/kg to about 140 mg/kg of body weight per day are useful in the treatment of psychiatric and mood disorders such as, for example, schizophrenia, anxiety, depression, panic, bipolar disorder, and circadian rhythm and sleep disorders—such as shift-work induced sleep disorder or jet-lag, as well as being useful in the treatment of pain which are responsive to mGluR5 inhibition, or alternatively about 0.5 mg to about 7 g per patient per day. For example, schizophrenia, anxiety, depression, panic, bipolar disorder, and circadian rhythm and sleep disorders—such as shift-work induced sleep disorder or jet-lag, may be effectively treated by the administration of from about 0.01 mg to 75 mg of the compound per kilogram of body weight per day, or alternatively about 0.5 mg to about 3.5 g per patient per day. Pain may be effectively treated by the administration of from about 0.01 mg to 125 mg of the compound per kilogram of body weight per day, or alternatively about 0.5 mg to about 5.5 g per patient per day. Further, it is understood that the mGluR5 inhibiting compounds of this invention can be administered at prophylactically effective dosage levels to prevent the above-recited conditions.

The amount of active ingredient that may be combined with the carrier materials to produce a single dosage form will vary depending upon the host treated and the particular mode of administration. For example, a formulation intended for the oral administration to humans may conveniently contain from about 0.5 mg to about 5 g of active agent, compounded with an appropriate and convenient amount of carrier material which may vary from about 5 to about 95 percent of the total composition. Unit dosage forms will generally contain between from about 1 mg to about 1000 mg of the active ingredient, typically 25 mg, 50 mg, 100 mg, 200 mg, 300 mg, 400 mg, 500 mg, 600 mg, 800 mg or 1000 mg.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound represented by Formula I, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient. Thus, a tablet, cachet, or capsule conveniently contains 0.1 mg, 1 mg, 5 mg, 25 mg, 50 mg, 100 mg, 200 mg, 300 mg, 400 mg, or 500 mg of the active ingredient taken one or two tablets, cachets, or capsules, once, twice, or three times daily.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

The compounds and pharmaceutical compositions of this invention have been found to exhibit biological activity as mGluR5 inhibitors. Accordingly, another aspect of the invention is the treatment in mammals of, for example, schizophrenia, anxiety, depression, panic, bipolar disorder, and circadian rhythm and sleep disorders—such as shift-work induced sleep disorder or jet-lag, pain, Parkinson's disease, cognitive dysfunction, epilepsy, drug addiction, drug abuse and drug withdrawal—maladies that are amenable to amelioration through inhibition of mGluR5—by the administration of an effective amount of the compounds of this invention. The term "mammals" includes humans, as well as other animals such as, for example, dogs, cats, horses, Figs, and cattle. Accordingly, it is understood that the treatment of mammals other than humans is the treatment of clinical correlating afflictions to those above recited examples that are human afflictions.

Further, as described above, the compound of this invention can be utilized in combination with other therapeutic compounds. In particular, the combinations of the mGluR5 inhibiting compound of this invention can be advantageously used in combination with i) opiate agonists or antagonists, ii) calcium channel antagonists, iii) 5HT receptor agonists or antagonists iv) sodium channel antagonists, v) NMDA receptor agonists or antagonists, vi) COX-2 selective inhibitors, vii) NK1 antagonists, viii) non-steroidal anti-inflammatory drugs ("NSAID"), ix) GABA-A receptor modulators, x) dopamine agonists or antagonists, xi) selective serotonin reuptake inhibitors ("SSRI") and/or selective serotonin and norepinephrine reuptake inhibitors ("SSNRI"), xii) tricyclic antidepressant drugs, xiii) norepinephrine modulators, xiv) L-DOPA, xv) buspirone, xvi) lithium, xvii) valproate, xviii) neurontin (gabapentin), xix) olanzapine, xx) nicotinic agonists or antagonists including nicotine, xxi) muscarinic agonists or antagonists, xxii) heroin substituting drugs such as methadone, levo-alpha-acetylmethadol, buprenorphine and naltrexone, and xxiii) disulfiram and acamprosate.

The abbreviations used herein have the following tabulated meanings. Abbreviations not tabulated below have their meanings as commonly used unless specifically stated otherwise.

| | |
|---|---|
| Ac | acetyl |
| AIBN | 2,2'-azobis(isobutyronitrile) |
| BINAP | 1,1'-bi-2-naphthol |
| Bn | benzyl |
| CAMP | cyclic adenosine-3',5'-monophosphate |
| DAST | (diethylamino)sulfur trifluoride |
| DEAD | diethyl azodicarboxylate |
| DBU | 1,8-diazabicyclo[5.4.0]undec-7-ene |
| DIBAL | diisobutylaluminum hydride |
| DMAP | 4-(dimethylamino)pyridine |
| DMF | N,N-dimethylformamide |
| dppf | 1,1'-bis(diphenylphosphino)-ferrocene |
| EDCI | 1-(3-dimethylaminopropyl)-3-ethylcarbodiimide hydrochloride |
| Et$_3$N | triethylamine |
| GST | glutathione transferase |
| HMDS | hexamethyldisilazide |
| LDA | lithium diisopropylamide |
| m-CPBA | metachloroperbenzoic acid |

-continued

| | |
|---|---|
| MMPP | monoperoxyphthalic acid |
| MPPM | monoperoxyphthalic acid, magnesium salt 6H$_2$O |
| Ms | methanesulfonyl = mesyl = SO$_2$Me |
| Ms0 | methanesulfonate = mesylate |
| NBS | N-bromo succinimide |
| NSAID | non-steroidal anti-inflammatory drug |
| o-Tol | ortho-tolyl |
| OXONE ® | 2KHSO$_5$.KHSO$_4$.K$_2$SO$_4$ |
| PCC | pyridinium chlorochromate |
| Pd$_2$(dba)$_3$ | Bis(dibenzylideneacetone) palladium(0) |
| PDC | pyridinium dichromate |
| PDE | Phosphodiesterase |
| Ph | Phenyl |
| Phe | Benzenediyl |
| PMB | para-methoxybenzyl |
| Pye | Pyridinediyl |
| r.t. | room temperature |
| Rac. | Racemic |
| SAM | aminosulfonyl or sulfonamide or SO$_2$NH$_2$ |
| SEM | 2-(trimethylsilyl)ethoxymethoxy |
| SPA | scintillation proximity assay |
| TBAF | tetra-n-butylammonium fluoride |
| Th | 2- or 3-thienyl |
| TFA | trifluoroacetic acid |
| TFAA | trifluoroacetic acid anhydride |
| THF | Tetrahydrofuran |
| Thi | Thiophenediyl |
| TLC | thin layer chromatography |
| TMS-CN | trimethylsilyl cyanide |
| TMSI | trimethylsilyl iodide |
| Tz | 1H (or 2H)-tetrazol-5-yl |
| XANTPHOS | 4,5-Bis-diphenylphosphanyl-9,9-dimethyl-9H-xanthene |
| C$_3$H$_5$ | Allyl |

| ALKYL GROUP ABBREVIATIONS | |
|---|---|
| Me = | Methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |
| c-Pr = | cyclopropyl |
| c-Bu = | cyclobutyl |
| c-Pen = | cyclopentyl |
| c-Hex = | cyclohexyl |

Assays Demonstrating Biological Activity

The compounds of this invention were tested against the hmGluR5a receptor stably expressed in mouse fibroblast Ltk$^-$ cells (the hmGluR5a/L38-20 cell line) and activity was detected by changes in [Ca$^{++}$]$_i$, measured using the fluorescent Ca$^{++}$-sensitive dye, fura-2. InsP assays were performed in mouse fibroblast Ltk$^-$ cells (LM5a cell line) stably expressing hmGluR5a. The assays described in International Patent Publication WO 0116121 can be used.

Calcium Flux Assay

The activity of compounds was examined against the hmGluR5a receptor stably expressed in mouse fibroblast Ltk-cells (the hmGluR5a/L38 cell line). See generally Daggett et al., *Neuropharmacology* 34:871-886 (1995). Receptor activity was detected by changes in intracellular calcium ([Ca$^{2+}$]$_i$) measured using the fluorescent calcium-sensitive dye, fura-2. The hmGluR5a/L38-20 cells were plated onto 96-well plates, and loaded with 3 µM fura-2 for 1 h. Unincorporated dye was washed from the cells, and the cell plate was transferred to a 96-channel fluorimeter (SIBIA-SAIC, La Jolla, Calif.) which is integrated into a fully automated plate handling and liquid delivery system. Cells were excited at 350 and 385 nm with a xenon source combined with optical filters. Emitted light was collected from the sample through a dichroic mirror and a 510 nm interference filter and directed into a cooled CCD camera (Princeton Instruments). Image pairs were captured approximately every 1 s, and ratio images were generated after background subtraction. After a basal reading of 20 s, an EC$_{80}$ concentration of glutamate (10 µM) was added to the well, and the response evaluated for another 60 s. The glutamate-evoked increase in [Ca']$_i$ in the presence of the screening compound was compared to the response of glutamate alone (the positive control).

Phosphatidylinositol Hydrolysis (PI) Assays

Inositolphosphate assays were performed as described by Berridge et al. [Berridge et al, *Biochem. J.* 206: 587-5950 (1982); and Nakajima et al., *J. Biol. Chem.* 267:2437-2442 (1992)] with slight modifications. Mouse fibroblast Ltk cells expressing hmGluR5 (hmGluR5/L38-20 cells) were seeded in 24-well plates at a density of 8×105 cells/well. One µCi of [$^3$H]-inositol (Amersham PT6-271; Arlington Heights, Ill.; specific activity=17.7 Ci/mmol) was added to each well and incubated for 16 h at 37° C. Cells were washed twice and incubated for 45 min in 0.5 mL of standard Hepes buffered saline buffer (HBS; 125 mM NaCl, 5 mM KCL 0.62 mM MgSO$_4$, 1.8 mM CaCl$_2$, 20 mM HEPES, 6 mM glucose, pH to 7.4). The cells were washed with HBS containing 10 mM LiCl, and 400 µL buffer added to each well. Cells were incubated at 37° C. for 20 min. For testing, 50 µL of 10× compounds used in the practice of the invention (made in HBS/LiCl (100 mM)) was added and incubated for 10 minutes. Cells were activated by the addition of 10 µM glutamate, and the plates left for 1 hour at 37° C. The incubations were terminated by the addition of 1 mL ice-cold methanol to each well. In order to isolate inositol phosphates (IPs), the cells were scraped from wells, and placed in numbered glass test tubes. One mL of chloroform was added to each tube, the tubes were mixed, and the phases separated by centrifugation. IPs were separated on Dowex anion exchange columns (AG 1-X8 100-200 mesh formate form). The upper aqueous layer (750 µL) was added to the Dowex columns, and the columns eluted with 3 mL of distilled water. The eluents were discarded, and the columns were washed with 10 mLs of 60 mM ammonium formate/5 mM Borax, which was also discarded as waste. Finally, the columns were eluted with 4 mL of 800 mM ammonium formate/0.1M formic acid, and the samples collected in scintillation vials. Scintillant was added to each vial, and the vials shaken, and counted in a scintillation counter after 2 hours. Phosphatidylinositol hydrolysis in cells treated with certain exemplary compounds was compared to phosphatidylinositol hydrolysis in cells treated with the agonist alone in the absence of compound.

The compounds of this application have mGluR5 inhibitory activity as shown by IC$_{50}$ values of less than 10 µM in the calcium flux assay or inhibition of >50% at a concentration of 100 µM in the PI assay. Preferably, the compounds should have IC$_{50}$ values of less than 1 µM in the calcium flux assay and IC$_{50}$ values of less than 10 µM in the PI assay. Even more preferably, the compounds should have IC$_{50}$ values of less than 100 nM in the calcium flux assay and IC$_{50}$ values of less than 1 µM in the PI assay.

Examples 1-22 have mGluR5 inhibitory activity as shown by IC$_{50}$ values of 10 μM or better in the calcium flux assay and/or inhibition of >50% at 100 μM concentration in the PI assay.

The examples that follow are intended as an illustration of certain preferred embodiments of the invention and no limitation of the invention is implied.

Unless specifically stated otherwise, the experimental procedures were performed under the following conditions. All operations were carried out at room or ambient temperature—that is, at a temperature in the range of 18-25° C. Evaporation of solvent was carried out using a rotary evaporator under reduced pressure (600-4000 pascals: 4.5-30 mm. Hg) with a bath temperature of up to 60° C. The course of reactions was followed by thin layer chromatography (TLC) and reaction times are given for illustration only. Melting points are uncorrected and 'd' indicates decomposition. The melting points given are those obtained for the materials prepared as described. Polymorphism may result in isolation of materials with different melting points in some preparations. The structure and purity of all final products were assured by at least one of the following techniques: TLC, mass spectrometry, nuclear magnetic resonance (NMR) spectrometry or microanalytical data. When given, yields are for illustration only. When given, NMR data is in the form of delta (δ) values for major diagnostic protons, given in parts per million (ppm) relative to tetramethylsilane (CMS) as internal standard, determined at 300 MHz, 400 MHz or 500 MHz using the indicated solvent. Conventional abbreviations used for signal shape are: s. singlet; d. doublet; t. triplet; m. multiplet; br. broad; etc. In addition, "Ar" signifies an aromatic signal. Chemical symbols have their usual meanings; the following abbreviations are used: v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

Methods of Synthesis

Compounds of the present invention can be prepared according to the following methods. The substituents are the same as in Formula I except where defined otherwise, or apparent to one in the art.

In accordance with another embodiment of the present invention, there are provided methods for the preparation of heteroaryl-substituted pyrrole compounds as described above. For example, many of the heterocyclic compounds described above can be prepared using synthetic chemistry techniques well known in the art (see *Comprehensive Heterocyclic Chemistry*, Katritzky, A. R. and Rees, C. W. eds., Pergamon Press, Oxford, 1984) from a heteoaryl-substituted pyrrole of Formula (I).

In Schemes 1 to 5 below, X and Y are as defined above. Other variables are understood by one in the art by the context in which they are used.

Scheme 1

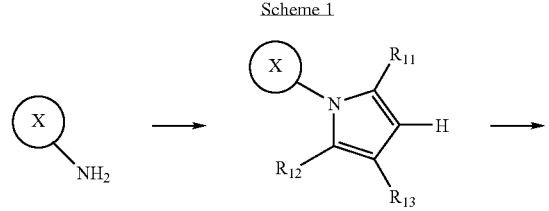

-continued

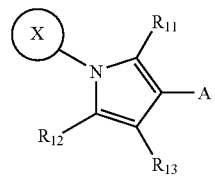

Thus in Scheme 1, ring system X containing an aniline moiety (prepared using synthetic chemistry techniques well known in the art) is reacted with a 1,4-dicarbonyl or its equivalent in a suitable solvent (e.g. EtOH, THF, DME, DMF etc.) at a temperature between 30° C. to 150° C. for 1 to 18 h to form a substituted pyrrole. In turn, the 3-position of the pyrrole is derivatized with a functional group A, such as a halogen or trifluoromethanesulfonate and the like, which is capable of undergoing a metal-catalyzed cross-coupling reaction. For example, the group A may be a bromine atom which may be installed using bromotrimethylsilane (see for example Pagnoni, U. G.; Pinetti, A. *J. Heterocycl. Chem.* 1993, 30, 617-621).

Scheme 2

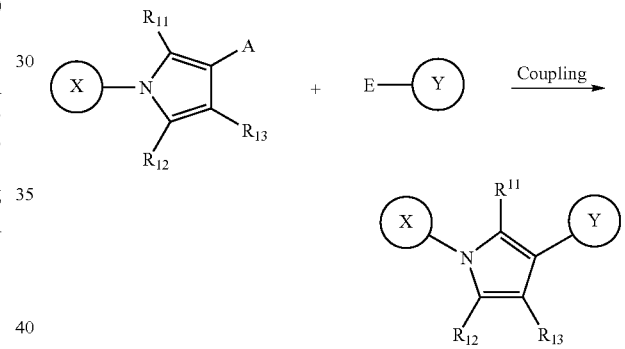

In turn, the derivatized pyrrole is reacted with a moiety Y under metal-catalyzed cross-coupling conditions (Scheme 2) where E is a metallic or metalloid species such as B(OR)$_2$, Li, MgHal, SnR$_3$, ZnHal, SiR$_3$ and the like which is capable of undergoing a metal-catalyzed cross-coupling reaction. The coupling may be promoted by a homogeneous catalyst such as Pd(PPh$_3$)$_4$, or by a heterogeneous catalyst such as Pd on carbon in a suitable solvent (e.g. THF, DME, toluene, MeCN, DMF, H$_2$O etc.). Typically a base, such as K$_2$CO$_3$, NEt$_3$, and the like, will also be present in the reaction mixture. Other promoters may also be used such as CsF. The coupling reaction is typically allowed to proceed by allowing the reaction temperature to warm slowly from about 0° C. up to rt over a period of several hours. The reaction mixture is then maintained at rt, or heated to a temperature anywhere between 30° C. to 150° C. The reaction mixture is then maintained at a suitable temperature for a time in the range of about 4 up to 48 h, with about 18 h typically being sufficient (see for example Miyaura, N.; Suzuki, A. *Chem. Rev.* 1995, 95, 2457-2483). The product from the reaction can be isolated and purified employing standard techniques, such as solvent extraction, chromatography, crystallization, distillation and the like. Another embodiment of the present invention is illustrated in Scheme 3.

Scheme 3

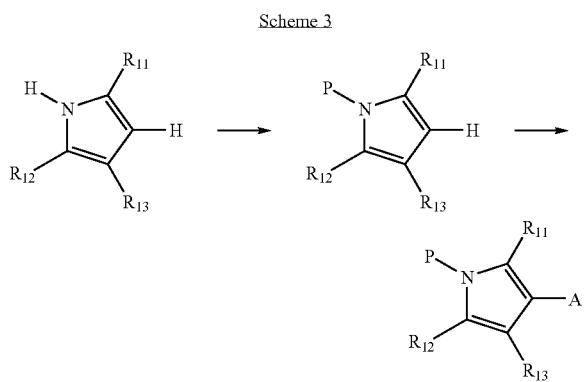

Thus, the free ring nitrogen in an optionally substituted pyrrole (prepared using synthetic chemistry techniques well known in the art) is protected with a group P, where P may be a trialkyl- or triaryl silane, arylsulfonyl or alkyl carbamate protecting group and the like. In turn, the 3-position of the pyrrole is derivatized with a functional group A, such as a halogen or trifluoromethanesulfonate and the like, which is capable of undergoing a metal-catalyzed cross-coupling reaction. For example, the group A may be an iodine which maybe installed using molecular iodine and mercuric acetate (see for example Bray, B. L. et al. *J. Org. Chem.* 1990, 55, 6317-6328).

Scheme 4

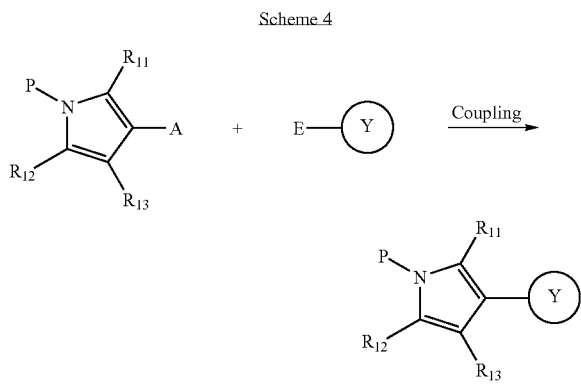

In turn, the derivatized pyrrole is reacted with a moiety Y under metal-catalyzed cross-coupling conditions (Scheme 4) where E is a metallic or metalloid species such as $B(OR)_2$, ZnHal, Li, MgHal, $SnR_3$, $SiR_3$ and the like which is capable of undergoing a metal-catalyzed cross-coupling reaction. The coupling may be promoted by a homogeneous catalyst such as $Pd(PPh_3)_4$, or by a heterogeneous catalyst such as Pd on carbon in a suitable solvent (e.g. THF, DME, toluene, MeCN, DMF, $H_2O$ etc.). If required a base, such as $K_2CO_3$, $NEt_3$, and the like, will also be present in the reaction mixture. Other promoters may also be used such as CsF. The coupling reaction is typically allowed to proceed by allowing the reaction temperature to warm slowly from about 0° C. up to rt over a period of several hours. The reaction mixture is then maintained at rt, or heated to a temperature anywhere between 30° C. to 150° C. The reaction mixture is then maintained at a suitable temperature for a time in the range of about 4 up to 48 h, with about 18 h typically being sufficient (see for example: Miyaura, N.; Suzuki, A. *Chem. Rev.* 1995, 95, 2457-2483 or Negishi, E.; Liu, F. Palladium or Nickel catalyzed Cross-coupling with Organometals Containing Zinc, Magnesium, Aluminium and Zirconium. In *Metal-catalyzed Cross-coupling Reactions* Diederich, F.; Stang, P. J. Eds. Wiley, Weinheim, Germany, 1998; pp1-42). The product from the reaction can be isolated and purified employing standard techniques, such as solvent extraction, chromatography, crystallization, distillation and the like.

Scheme 5

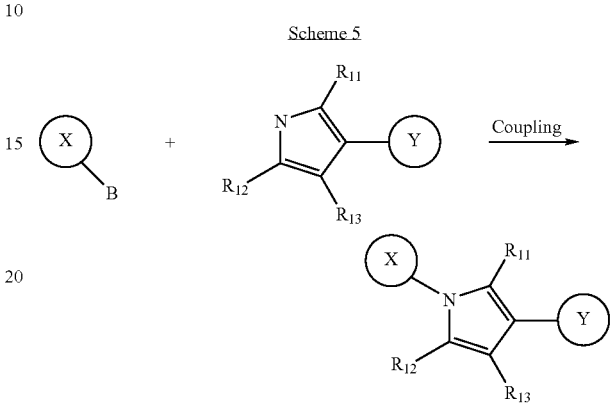

As shown in Scheme 5, the pyrrole may then be coupled with a species X substituted with a group B. B may be a good aryl leaving group such as P, and X is electron deficient or has one or more electron withdrawing substituents (e.g. $NO_2$, CN etc.), the coupling reaction may be effected thermally in a temperature range of about 60° C. up to about 250° C. Typically, this reaction is carried out in the presence of base (e.g. pyridine, $NEt_3$, $Cs_2CO_3$, $K_2CO_3$ etc.) in a suitable solvent, such as DMSO, DMF, DMA $H_2O$ and the like, and takes from 1 h up to about 72 h with 18 h typically being sufficient (see for example Russell, S. S.; Jahangir; *Synth. Commun.* 1994, 24, 123-130).

Alternatively, B may be a good leaving group capable of undergoing a metal-catalyzed cross-coupling reaction such as a halogen or trifluoromethanesulfonate and the like. Typically, the reaction is carried out using catalytic amounts of a copper (I) salt together with a diamine ligand and in the presence of a suitable base (e.g. $K_3PO_4$, $Cs_2CO_3$, $K_2CO_3$ etc.) in a suitable solvent, such as Dioxane, DMSO, DMA, DMF (see for example Klapers, A.; Antilla, J. C.; Huang, X.; Buchwald, S. L *J. Am. Chem Soc.* 2001, in press).

In addition, many of the heterocyclic compounds described above can be prepared using other synthetic chemistry techniques well known in the art (see *Comprehensive Heterocyclic Chemistry*, Katritzky, A. R. and Rees, C. W. eds., Pergamon Press, Oxford, 1984) and references cited there within.

COMPOUND 1

Synthesis of 2-(3-bromo-1H-pyrrol-1-yl)pyridine

Bromotrimethylsilane (10.9 mL, 84 mmol) was added to DMSO (5.7 mL, 84 mmol) in MeCN (200 mL) at 0° C. After stirring for 10 min, 2-(1H-pyrrol-1-yl)pyridine (10 g, 70 mmol) in MeCN (50 mL) was added. The reaction mixture was stirred at 0° C. and allowed to reach rt over 3 h. $H_2O$ (150 mL) and EtOAc (150 mL) were added and the reaction mixture was shaken, the EtOAc layer was separated and the aqueous layer shaken with EtOAc (3×150 mL). The combine organic layers were dried over $Na_2SO_4$ and concentrated to a brown oil. LCMS indicated good conversion to 2-(3-bromo-1H-pyrrol-1-yl)pyridine and this was used without further purification. (MS (ESI) 224 (M+H)$^+$.

EXAMPLE 1

Synthesis of 3-(1-pyridin-2-yl-1H-pyrrol-3-yl)benzonitrile 2-(3-Bromo-1H-pyrrol-1-yl)pyridine (1.34 g, 2 mmol), 3-cyanophenylboronic acid (0.59 g, 4 mmol), Pd(PPh$_3$)$_4$ (116 mg, 0.1 mmol) and potassium carbonate (560 mg, 4 mmol) were dissolved in a mixture of DME (18 mL) and H$_2$O (2 mL) and degassed for 15 min with Ar (g). The reaction mixture was then heated at 84° C. for 18 h. At this time, a further 0.25 eq. of 3-cyanophenylboronic acid (0.15 g, 1 mmol) was added and heating was continued. After a total of 42 h, the reaction mixture was cooled to rt, H$_2$O (40 mL) and EtOAc (40 mL) were added and the reaction mixture shaken, the EtOAc layer was separated and the aqueous layer shaken with EtOAc (2×30 mL). The combined organic layers were dried over Na$_2$SO$_4$ and concentrated to a yellow oil. This was purified by liquid chromatography on silica gel eluting with EtOAc:hexane (3:7) to afford a white waxy solid that was further purified by liquid chromatography on silica gel eluting with dichloromethane to afford 3-(1-pyridin-2-yl-1H-pyrrol-3-yl)benzonitrile as a colorless oil. $^1$H NMR (CD$_3$Cl, 300 MHz) δ 8.49-8.52 (1H, m), 7.66 (1H, ddd), 7.47-7.51 (2H, m), 7.33-7.39 (3H, m), 7.24 (1H, ddd), 6.91 (1H, d), 6.51-6.52 (1H, m), 6.43 (1H, dd). MS (ESI) 246 (M+H)$^+$.

EXAMPLE 2

Synthesis of 2-[3-(3-chlorophenyl)-1H-pyrrol-1-yl]pyridine 2-(3-Bromo-1H-pyrrol-1-yl)pyridine (1.34 g, 2 mmol), 3-chlorophenylboronic acid (0.62 g, 4 mmol), Pd(PPh$_3$)$_4$ (116 mg, 0.1 mmol) and potassium carbonate (560 mg, 4 mmol) were dissolved in a mixture of DME (18 mL) and H$_2$O (2 mL) and degassed for 15 min with Ar (g). The reaction mixture was then heated at 84° C. for 18 h. At this time, a further 0.25 eq. of 3-chlorophenylboronic acid (0.16 g, 1 mmol) was added and heating was continued. After a total of 42 h, the reaction mixture was cooled to rt, H$_2$O (40 mL) and EtOAc (40 mL) were added and the reaction mixture shaken, the EtOAc layer was separated and the aqueous layer shaken with EtOAc (2×30 mL). The combined organic layers were dried over Na$_2$SO$_4$ and concentrated to a yellow oil. This was purified by liquid chromatography on silica gel eluting with EtOAc:hexane (3:7) to afford a white solid that was further purified by preparative HPLC to afford 2-[3-(3-chlorophenyl)-1H-pyrrol-1-yl]pyridine as a white solid. $^1$H NMR (CD$_3$Cl, 300 MHz) δ 8.52-8.54 (1H, m), 7.61 (1H, ddd), 7.35-7.37 (1H, m), 7.28 (1H, s), 7.15-7.24 (3H, m), 6.99 (1H, ddd), 6.86 (1H, d), 6.47-6.48 (1H, m), 6.41 (1H, dd).). MS (ESI) 255 (M+H)$^+$.

EXAMPLE 3

Synthesis of 2-[3-(3-methoxyphenyl)-1H-pyrrol-1-yl]pyridine 2-(3-Bromo-1H-pyrrol-1-yl)pyridine (1.34 g, 2 mmol), 3-methoxyphenylboronic acid (0.61 g, 4 mmol), Pd(PPh$_3$)$_4$ (116 mg, 0.1 mmol) and potassium carbonate (560 mg, 4 mmol) were dissolved in a mixture of DME (18 mL) and H$_2$O (2 mL) and degassed for 15 min with Ar (g). The reaction mixture was then heated at 84° C. for 18 h. At this time, a further 0.25 eq. of 3-methoxyphenylboronic acid (0.15 g, 1 mmol) was added and heating was continued. After a total of 42 h, the reaction mixture was cooled to rt, H$_2$O (40 mL) and EtOAc (40 mL) were added and the reaction mixture shaken, the EtOAc layer was separated and the aqueous layer shaken with EtOAc (2×30 mL). The combined organic layers were dried over Na$_2$SO$_4$ and concentrated to a yellow oil. This was purified by liquid chromatography on silica gel eluting with EtOAc:hexane (3:7) to afford a white solid that was further purified by preparative HPLC to afford 2-[3-(3-methoxyphenyl)-1H-pyrrol-1-yl]pyridine as a white solid. $^1$H NMR (CD$_3$Cl, 300 MHz) δ 8.52-8.54 (1H, m), 7.55 (1H, ddd), 7.38-7.39 (1H, m), 7.15-7.21 (2H, m), 6.76-6.85 (4H, m), 6.46-6.48 (1H, m), 6.41 (1H, dd). MS (ESI) 251 (M+H)$^+$.

COMPOUND 2

Synthesis of 3-iodo-1-(triisopropylsilyl)-1H-pyrrole

3-Iodo-1-(triisopropylsilyl)-1H-pyrrole was prepared according to the method of Bray, B. L. et al. *J. Org. Chem.* 1990, 55, 6317-6328.

COMPOUND 3

Synthesis of 2-[1-(triisopropylsilyl)-1H-pyrrol-3-yl]pyridine

A solution of 3-iodo-1-(triisopropylsilyl)-1H-pyrrole (11.0 g, 2.87 mmol), triphenylphosphine (27 mg, 0.103 mmol), and tetrakis(triphenylphosphine)palladium(0) (80 mg, 0.069 mmol) in THF (20 mL) was degassed with Ar (g) for 15 min, then 2-bromo(pyridin-2-yl)zinc (1.5 mL of 0.5M solution, 5.74 mmol) was added and degassing continued a further 15 min. The reaction was stirred at 70° C. for 5 h and monitored by LC/MS. The reaction mixture was quenched with H$_2$O (40 mL) then extracted with EtOAc (3×25 mL) and the combined organic extracts washed with brine. The organic phase was dried over Na$_2$SO$_4$, concentrated in vacuo and the crude residue was chromatographed on silica gel eluting with EtOAc:hexane (1:9) to afford 2-[1-(triisopropylsilyl)-1H-pyrrol-3-yl]pyridine as a clear oil which was used below without further purification.

COMPOUND 4

Synthesis of 2-(1H-pyrrol-3-yl)pyridine

To a solution of 2-[1-(triisopropylsilyl)-1H-pyrrol-3-yl]pyridine (1 g, 3.2 mmol) in anhydrous THF (15 mL) was added TBAF (3.84 mL of a 1M solution in THF, 3.84 mmol). After stirring for 10 min. at rt, the reaction was complete. The reaction mixture quenched with H$_2$O (40 mL), extracted with EtOAc (3×25 mL) and the combined organic extracts washed with brine. The organic phase was dried over Na$_2$SO$_4$, concentrated in vacuo and chromatographed on silica gel eluting with EtOAc:hexane (1:1) to afford 2-(1H-pyrrol-3-yl)pyridine as a solid. $^1$H NMR (CD$_3$Cl, 300 MHz) δ 8.55 (ddd, 1H), 7.65 (dt, 1H), 7.54 (dd, 1H), 7.46~7.43 (d, 1H), 7.07 (ddd, 1H), 6.85 (dd, 1H), 6.74 (dd, 1H). MS (ESI) 145.1 (M$^+$+H).

EXAMPLE 4

Synthesis of
3-(3-pyridin-2-yl-1H-pyrrol-1-yl)benzonitrile 2-(1H-Pyrrol-3-yl)pyridine (0.144 g, 11.0 mmol), 3-fluorobenzonitrile (1.21 g, 10 mmol), and potassium carbonate (0.0.276 g, 2 mmol) were heated at 145° C. in DMF (0.5 mL) for 14 h. After this time, the reaction mixture was cooled to rt and quenched with $H_2O$ (30 mL). The mixture was extracted with EtOAc (3×25 mL) and the combined organic extracts washed with brine. The organic phase was dried over $Na_2SO_4$, concentrated in vacuo and the residue was chromatographed on silica gel eluting with EtOAc:hexane (2:3) to afford a white solid which was recrystallized from dichloromethane-hexane to give 3-(3-pyridin-2-yl-1H-pyrrol-1-yl)benzonitrile as white crystals. $^1$H NMR ($CD_3Cl$, 300 MHz) δ 8.59 (ddd, 1H), 7.78~7.71 (m, 3H), 7.68 (dd, 1H), 7.62~7.53 (m, 3H), 7.17~7.11 (m, 2H), 6.89 (dd, 1H). MS (ES) 246.1 ($M^+$+H).

EXAMPLE 5

Synthesis of 2-{1-[3-(trifluoromethyl)phenyl]-1H-pyrrol-3-yl}pyridine hydrochloride Following the procedure described in EXAMPLE 4,2-(1H-pyrrol-3-yl)pyridine (0.072 g, 0.50 mmol), 1-fluoro-3-(trifluoromethyl)benzene (0.82 g, 5.0 mmol), and potassium carbonate (0.138 g, 1.0 mmol) were employed to obtain 2-{1-[3-(trifluoromethyl)phenyl]-1H-pyrrol-3-yl}pyridine hydrochloride as an orange solid. $^1$H-NMR ($CD_3OD$, 300 MHz) 8.60 (d, 1H), 8.49-8.46 (m, 2H), 8.36 (d, 1H), 7.98-7.94 (m, 2H), 7.80-7.71 (m, 3H), 7.62 (t, 1H), 7.13 (dd, 1H). MS (EI) 289.0 ($M^+$+H).

EXAMPLE 6

Synthesis of
2-[1-(3,5-dichlorophenyl)-1H-pyrrol-3-yl]pyridine
hydrochloride

A solution of 2-(1H-pyrrol-3-yl)pyridine (0.072 g, 0.5 mmol), 1,3-dichloro-5-iodobenzene (0.163 g, 0.6 mmol), 1,10-phenanthroline (0.360 g, 2 mmol) and potassium phosphate (0.223 g, 1.05 mmol) in dioxane were degassed for 10 min, then copper (I) iodide (0.038 g, 0.2 mmol) was added and the mixture degassed a further 10 min. The mixture was heated to 110° C. for 4 h. The reaction mixture was quenched with brine, extracted with EtOAc (3×25 mL) and the combined organic extracts washed with brine. The organic phase was dried over $Na_2SO_4$, concentrated in vacuo and the residue was chromatographed on silica gel eluting with EtOAc:hexane (1:4) to afford a white solid. The crude material was dissolved in THF (5 mL), 1.2 eq. of 1M HCl in diethyl ether was added and the resulting precipitate was filtered to obtain 2-[1-(3,5-dichlorophenyl)-1H-pyrrol-3-yl]pyridine hydrochloride as a white solid. $^1$H-NMR ($CD_3OD$, 300 MHz) δ 8.60 (d, 1H), 8.50 (dd, 1H), 8.41 (dd, 1H), 8.34 (d, 1H), 7.80-7.69 (m, 3H), 7.59 (dd, 1H), 7.50-7.49 (m, 1H), 7.11-7.09 (dd, 1H). MS (ESI) 289.0 ($M^+$+H).

EXAMPLE 7

Synthesis of
2-[1-(3-methylphenyl)-1H-pyrrol-3-yl]pyridine
hydrochloride

Following the procedure described in EXAMPLE 6,2-(1H-pyrrol-3-yl)pyridine (0.072 g, 0.50 mmol) 1-iodo-3-methylbenzene (0.130 g, 0.6 mmol), 1,10-phenanthroline (0.360 g, 2 mmol) and potassium phosphate (0.223 g, 1.05 mmol) and copper (I) iodide (0.038 g, 0.2 mmol) were employed to obtain 2-[1-(3-methylphenyl)-1H-pyrrol-3-yl]pyridine. Treatment of this material with 1.2 eq of 1M HCl in diethyl ether provided 2-[1-(3-methylphenyl)-1H-pyrrol-3-yl]pyridine hydrochloride as a white solid. $^1$H-NM ($CD_3OD$, 300 MHz) δ 8.46 (d, 1H), 8.35 (dd, 1H), 8.24-8.20 (m, 21), 7.65-7.60 (m, 1H), 7.41-7.38 (m, 2H), 7.34-7.32 (m, 2H), 7.17-7.14 (m, 1H), 6.97 (dd, 1H), 2.37 (s, 3H). MS (ESI) 235.3 ($M^+$+H).

EXAMPLE 8

Synthesis of
2-[1-(3-methoxyphenyl)-1H-pyrrol-3-yl]pyridine
hydrochloride

Following the procedure described in EXAMPLE 6,2-(1H-pyrrol-3-yl)pyridine (0.072 g, 0.50 mmol) 1-bromo-3-methoxybenzene (0.113 g, 0.6 mmol), 1,10-phenanthroline (0.360 g, 2 mmol) and potassium phosphate (0.223 g, 1.05 mmol) and copper (I) iodide (0.038 g, 0.2 mmol) were employed to obtain 2-[1-(3-methoxyphenyl)-1H-pyrrol-3-yl]pyridine. Treatment of this material with 1.2 eq. of 1M HCl in diethyl ether provided 2-[1-(3-methoxyphenyl)-1H-pyrrol-3-yl]pyridine hydrochloride as a white solid. $^1$H-NMR ($CD_3OD$, 300 MHz) δ 8.55 (d, 1H), 8.45 (dd, 1H), 8.33-8.29 (m, 2H), 7.74-7.69 (m, 1H), 7.51 (dd, 1H), 7.48-7.42 (m, 1H), 7.21-7.17 (m, 2H), 7.04 (dd, 1H), 7.00-6.97 (m, 1H), 3.89 (s, 3H). MS (ESI) 251.1 ($M^+$+H).

COMPOUND 5

Synthesis of 2-[1-(triisopropylsilyl)-1H-pyrrol-3-yl]-1,3-thiazole

To a solution of 3-bromo-1-(triisopropylsilyl)-1H-pyrrole (0.691 g, 2.28 mmol) in THF (10 mL) at −78° C. was added t-butyllithium (2.83 mL, 4.80 mmol of 1.7M solution in heptane). The solution was stirred at −78° C. for 45 min, then trimethylborate (2.38 g, 22.8 mmol) was added and stirred at −78° C. for 20 min. The reaction mixture was allowed to warm to rt and then cooled again to −78° C. before methanol:water (V:V=1:1, 0.9 mL) was added and the solution allowed warm to rt. The reaction mixture was quenched with brine (10 mL) and extracted with EtOAc (3×25 mL). The combined organic phase was washed with brine, dried over $Na_2SO_4$ and concentrated in vacuo to give crude 1-(triisopropylsilyl)-1H-pyrrol-3-ylboronic acid which was used without further purification.

A solution of crude 1-(triisopropylsilyl)-1H-pyrrol-3-ylboronic acid, 2-bromo-1,3-thiazole (0.206 g, 1.26 mmol) and potassium carbonate (0.174 g, 1.26 mmol) in benzene (10 mL), methanol (1 mL) and water (1 mL) was degassed with argon for 15 min. Tetrakis(triphenylphosphine)palladium(0) (40 mg, 0.034 mmol) was added and the reaction mixture was degassed a further 15 min before stirring at 70° C. for 14 h. The reaction mixture was quenched with water (30 mL) then extracted with EtOAc (3×30 mL) and washed with brine. The combined organic phase was dried over $Na_2SO_4$ and concentrated in vacuo. The crude residue was chromatographed on silica gel eluting with EtOAc:hexane (1:1) to afford 2-[1-(triisopropylsilyl)-1H-pyrrol-3-yl]-1,3-thiazole as a brown oil. $^1$H NMR ($CD_3Cl$, 300 MHz) δ 7.68 (d, 1H), 7.37-7.36 (m, 1H), 7.08 (d, 1H), 7.76-7.75 (m, 1H), 6.70 (dd, 1H), 1.46 (h, 3H) 1.09 (d, 18H).

COMPOUND 6

Synthesis of 2-(1H-pyrrol-3-yl)-1,3-thiazole

To a solution of 2-[1-(triisopropylsilyl)-1H-pyrrol-3-yl]-1,3-thiazole (0.200 g, 0.671 mmol) in anhydrous THF (2 mL) was added TBAF (1 mL, 1 mmol of a 1M in THF) and after stirring for 20 min at rt, the reaction was complete. The reaction mixture was quenched with water (40 mL), extracted with EtOAc (3×25 mL) and washed with brine.

The organic phase was dried over Na₂SO₄, concentrated in vacuo and chromatographed on silica gel eluting with EtOAc:hexane (1:1) to afford 2-(1H-pyrrol-3-yl)-1,3-thiazole as a pale solid. $^1$H NMR (CD₃Cl, 300 MHz) δ 8.20 (br, 1H) 7.63 (d, 1H), 7.28 (d, 1H), 7.06 (d, 1H), 6.73 (dd, 1H), 6.57 (dd, 1H).

EXAMPLE 9

Synthesis of 3-[3-(1,3-thiazol-2-yl)-1H-pyrrol-1-yl]benzonitrile

Following the procedure described in EXAMPLE 4,2-(1H-pyrrol-3-yl)-1,3-thiazole (0.100 g, 0.66 mmol), 1-fluoro-3-(trifluoromethyl)benzene (0.805 g, 6.66 mmol), and potassium carbonate (0.183 g, 1.33 mmol) were employed to obtain 3-[3-(1,3-thiazol-2-yl)-1H-pyrrol-1-yl]benzonitrile. Treatment of this material with 1.2 eq. of 1M HCl in diethyl ether provided 3-[3-(1,3-thiazol-2-yl)-1H-pyrrol-1-yl]benzonitrile hydrochloride as a pale solid. $^1$H-NMR (CD₃OD, 300 MHz) δ 8.42 (t, 1H), 8.14-8.11 (m, 2H), 8.03-7.97 (m, 1H), 7.90 (m, 1H), 7.81-7.71 (m, 2H), 7.63 (dd, 1H), 7.03 (d, 1H). MS (ESI) 252.1 (M⁺+H).

EXAMPLE 10 to EXAMPLE 22 shown below were prepared similarly to the schemes and procedures described above (ND=not determined).

| Example | Structure | $^1$H NMR | MS (ESI) | NAME |
|---|---|---|---|---|
| 10 | 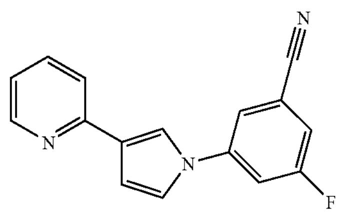 | 8.58-8.57 (dd, 1H), 7.74-7.73 (m, 1H), 7.69-7.66 (m, 1H), 7.56 (br, 1H), 7.53-7.51 (d, 1H), 7.45-7.42 (m, 1H), 7.26-7.24 (m, 1H), 7.13-7.11 (m, 2H), 6.89-6.88 (m, 1H). | MS 265.1 (M⁺ + H). | 3-fluoro-5-(3-pyridin-2-yl-1H-pyrrol-1-yl)benzonitrile |
| 11 | 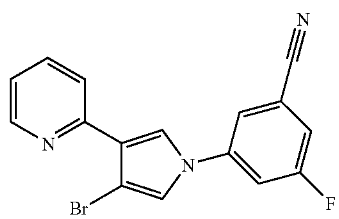 | 8.62-8.61 (d, 1H), 7.99-7.98 (d, 1H), 7.77-7.73 (m, 1H), 7.69-7.68 (d, 1H), 7.54 (s, 1H), 7.43-7.41 (m, 1H), 7.30-7.28 (m, 1H), 7.22 7.20 (m, 2H). | MS 342.15 (M⁺ + H). | 3-(3-bromo-4-pyridin-2-yl-1H-pyrrol-1-yl)-5-fluorobenzonitrile |
| 12 | 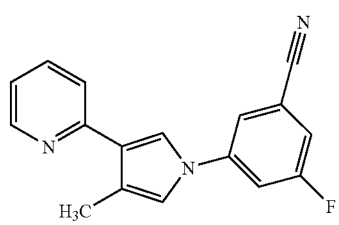 | 8.62-8.61 (m, 1H), 7.71-7.67 (m, 1H), 7.58-7.57 (d, 1H), 7.51-7.49 (m, 2H), 7.39-7.36 (m, 1H), 7.20-7.18 (m, 1H), 7.15-7.13 (m, 1H), 6.934-6.927 (m, 1H), 2.39 (s, 1H). | MS 278.61 (M⁺ + H). | 3-fluoro-5-(3-methyl-4-pyridin-2-yl-1H-pyrrol-1-yl)benzonitrile |
| 13 | 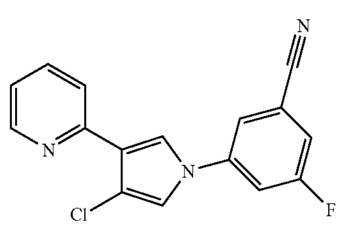 | 8.68-8.67 (d, 1H), 7.82-7.80 (d, 1H), 7.75-7.71 (m, 1H), 7.58 (s, 1H), 7.48-7.43 (m, 2H), 7.20-7.17 (m, 1H), 6.934-6.928 (d, 1H), 6.90-6.89 (d, 1H). | MS 298.33 (M⁺ + H). | 3-(3-chloro-4-pyridin-2-yl-1H-pyrrol-1-yl)-5-fluorobenzonitrile |
| 14 | 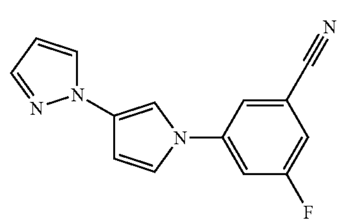 | 7.74 (d, 1H), 7.66 (d, 1H), 7.51 (s, 1H), 7.37-7.40 (m, 2H), 7.26 (m, 1H), 7.10 (dd, 1H), 6.63 (m, 1H), 6.42 (dd, 1H). | MS 253.3 (M⁺ + H). | 3-fluoro-5-[3-(1H-pyrazol-1-yl)-1H-pyrrol-1-yl]benzonitrile |

-continued

| Example | Structure | ¹H NMR | MS (ESI) | NAME |
|---|---|---|---|---|
| 15 | 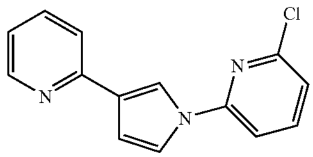 | 8.59 (d, 1H), 8.13 (dd, 1H), 7.74 (dd, 1H), 7.68 (m, 1H), 7.56-7.61 (m, 2H), 7.31 (d, 1H), 7.16 (d, 1H), 7.12 (m, 1H), 6.88 (m, 1H). | MS 256.4 (M⁺ + H). | 2-chloro-6-(3-pyridin-2-yl-1H-pyrrol-1-yl)pyridine |
| 16 | 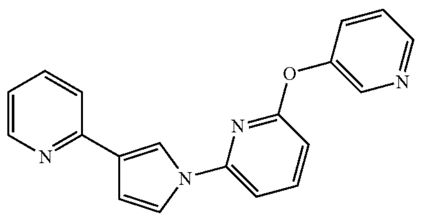 | N/A | MS 315.3 (M⁺ + H). | 2-(pyridin-3-yloxy)-6-(3-pyridin-2-yl-1H-pyrrol-1-yl)pyridine |
| 17 | 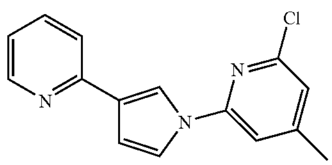 | 8.57 (d, 1H), 8.09 (m, 1H), 7.66 (m, 1H), 7.54-7.58 (m, 2H), 7.08-7.11 (m, 2H), 6.99 (s, 1H), 6.84 (dd, 1H), 2.40 (s, 3H). | MS 270.7 (M⁺ + H). | 2-chloro-4-methyl-6-(3-pyridin-2-yl-1H-pyrrol-1-yl)pyridine |
| 18 | 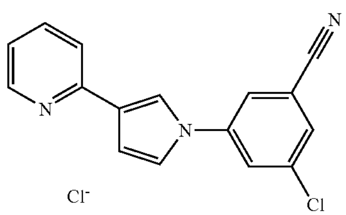 | 8.87-8.86 (d, 1H), 8.65-8.66 (d, 1H), 8.44-8.46 (m, 1H), 8.27-8.30 (m, 3H), 8.03 (s, 1H), 7.85 (s, 1H), 7.70-7.72 (m, 1H), 7.39(s, 1H). | MS 280.1 (M⁺ + 2H). | 3-chloro-5-(3-pyridin-2-yl-1H-pyrrol-1-yl)benzonitrile |
| 19 | 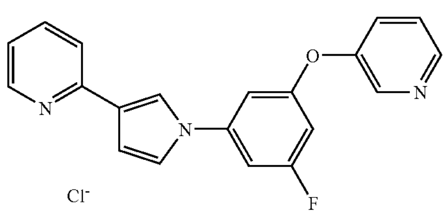 | 8.87 (s, 1H), 8.70-8.71 (d, 1H), 8.59-8.60 (d, 1H), 8.55-8.50 (m, 2H), 8.39-8.41 (d, 1H), 8.34-8.36 (d, 1H)8.12-8.14 9 (m, 1H), 7.76-7.78 (m, 1H), 7.62 (s, 1H), 7.53 (s, 1H), 7.51 (s, 1H), 7.10-7.14 (m, 2H) | MS 333.1 (M⁺ + 1H). | 2-{1-[3-fluoro-5-(pyridin-3-yloxy)phenyl]-1H-pyrrol-3-yl}pyridine |
| 20 | 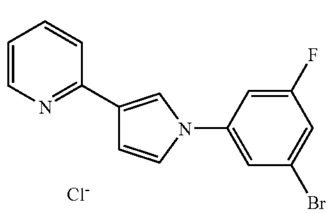 | 8.61-8.62 (d, 1H), 8.50-8.53 (m, 1H), 8.40-8.41(m, 1H), 8.35-8.36 (d, 1H), 7.9-7.81 (m, 2H), 7.61-7.62 (m, 1H), 7.54-7.57 (d, 1H), 7.42-7.46 (d, 1H), 7.11-7.12 (m, 1H). | MS 319.0 (M⁺ + 2H). | 3-bromo-5-(3-pyridin-2-yl-1H-pyrrol-1-yl)benzonitrile |
| 21 | 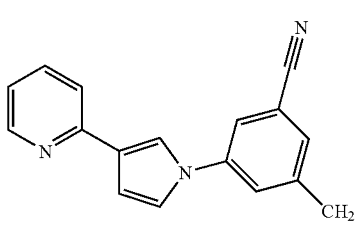 | 8.56-8.57 (d, 1H), 7.73-7.74 (d, 1H), 7.65-7.68 (m, 1H), 7.51-7.54 (m, 3H), 7.36 (s, 1H), 7.09-7.12(m, 2H), 6.84-6.86 (m, 1H). | MS 259.3 (M⁺ + H). | 3-methyl-5-(3-pyridin-2-yl-1H-pyrrol-1-yl)benzonitrile |

-continued

| Example | Structure | ¹H NMR | MS (ESI) | NAME |
|---|---|---|---|---|
| 22 | 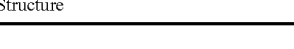 | 8.79-8.78 (d, 1H), 7.674-7.666 (m, 1H), 8.5 (s, 1H), 7.44-7.41 (m, 1H), 7.31-7.29 (m, 1H), 7.25-7.24 (d, 1H), 7.13-7.12 (m, 1H), 6.855-6.846 (m, 1H). | MS 252.1 (M⁺ + H). | 3-fluoro-5-[3-(1,3-thiazol-2-yl)-1H-pyrrol-1-yl]benzonitrile |

Other variations or modifications, which will be obvious to those skilled in the art, are within the scope and teachings of this invention. This invention is not to be limited except as set forth in the following claims.

What is claimed is:

1. A compound of the Formula (I):

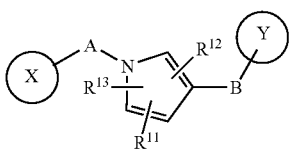

wherein:

X and Y each independently is aryl or heteroaryl wherein at least one of X and Y is a heteroaryl with N adjacent to the position of attachment to A or B respectively;

X is optionally substituted with 1-7 independent halogen, —CN, NO$_2$, —C$_{1-6}$alkyl, —C$_{1-6}$alkenyl, —C$_{1-6}$alkynyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(=NR$^1$)R$^2$, or —C(=NOR$^1$)R$^2$ substituents, wherein optionally two substituents are combined to form a cycloalkyl or heterocycloalkyl ring fused to X; wherein the —C$_{1-6}$alkyl substituent, cycloalkyl ring, or heterocycloalkyl ring each optionally is further substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) groups;

R$^1$, R$^2$, and R$^3$ each independently is —C$_{0-6}$alkyl, —C$_{3-7}$cycloalkyl, heteroaryl, or aryl; any of which is optionally substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

R$^4$ is C$_{1-6}$alkyl, —C$_{3-7}$cycloalkyl, heteroaryl, or aryl; optionally substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

A is —C$_{0-4}$alkyl, —C$_{0-2}$alkyl-SO—C$_{0-2}$alkyl-, —C$_{0-2}$alkyl-SO$_2$—C$_{0-2}$alkyl-, —C$_{0-2}$alkyl-CO—C$_{0-2}$alkyl-, —C$_{0-2}$alkyl-NR$^9$CO—C$_{0-2}$alkyl-, —C$_{0-2}$alkyl-NR$^9$SO$_2$-C$_{0-2}$alkyl or heteroC$_{0-4}$alkyl;

Y is optionally substituted with 1-7 independent halogen, —CN, NO$_2$, —C$_{1-6}$alkyl, —C$_{1-6}$alkenyl, —C$_{1-6}$alkynyl, —OR$^5$, —NR$^5$R$^6$, —C(=NR$^5$)NR$^6$R$^7$, —N(=NR$^5$)NR$^6$R$^7$, —NR$^5$COR$^6$, —NR$^5$CO$_2$R$^6$, —NR$^5$SO$_2$R$^8$, —NR$^5$CONR$^6$R$^7$, —SR$^8$, —SOR$^8$, —SO$_2$R$^8$, —SO$_2$NR$^5$R$^6$, —COR$^5$, —CO$_2$R$^5$, —CONR$^5$R$^6$, —C(=NR$^5$)R$^6$, or —C(=NOR$^5$) R$^6$substituents, wherein optionally two substituents are combined to form a cycloalkyl or heterocycloalkyl ring fused to Y; wherein the C$_{1-6}$alkyl substituent, cycloalkyl ring, or heterocycloalkyl ring each optionally is further substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) groups;

R$^5$, R$^6$, and R$^7$ each independently is —C$_{0-6}$alkyl, —C$_{3-7}$cycloalkyl, heteroaryl, or aryl; any of which is optionally substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

R$^8$ is —C$_{1-6}$alkyl, —C$_{3-7}$cycloalkyl, heteroaryl, or aryl; optionally substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

B is —C$_{0-4}$alkyl, —C$_{0-2}$alkyl-SO—C$_{0-2}$alkyl-, —C$_{0-2}$alkyl-SO$_2$—C$_{0-2}$alkyl-, —CO$_2$alkyl-CO—C$_{0-2}$alkyl-, C$_{0-2}$alkyl-NR$^{10}$CO—C$_{0-2}$alkyl-, —C$_{0-2}$alkyl-NR$^{10}$SO$_2$C$_{0-2}$alkyl or heteroC$_{0-4}$alkyl;

R$^9$ and R$^{10}$ each independently is —C$_{0-6}$alkyl, —C$_{3-7}$cycloalkyl, heteroaryl, or aryl; any of which is optionally substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

R$^{11}$, R$^{12}$ and R$^{13}$ is each independently halogen, —C$_{0-6}$alkyl, —C$_{0-6}$alkoxyl, =O, =N(C$_{0-4}$alkyl),or —N(C$_{0-4}$alkyl)(C$_{0-4}$alkyl), wherein optionally two of R$^{11}$, R$^{12}$ and R$^{13}$ are combined to form a cycloalkyl, heterocycloalkyl, aryl or heteroaryl ring fused to the pyrrole moiety; wherein the —C$_{1-6}$alkyl substituent, cycloalkyl ring, or heterocycloalkyl ring each optionally is further substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) groups;
any N may be an N-oxide; and
wherein any of the alkyl optionally is substituted with 1-9 independent halogens;
or a pharmaceutically acceptable salt thereof.

2. The compound of claim 1 wherein:
X is 2-pyridyl optionally substituted with 1-4 independent halogen, —CN, NO$_2$, —C$_{1-6}$alkyl, —C$_{1-6}$alkenyl, —C$_{1-6}$alkynyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(=NR$^1$)R$^2$, or —C(=NOR$^1$)R$^2$ substituents, wherein optionally two substituents are combined to form a cycloalkyl or heterocycloalkyl ring fused to X; wherein the —C$_{1-6}$alkyl substituent, cycloalkyl ring, or heterocycloalkyl ring each optionally is further substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) groups.

3. The compound of claim 2 wherein:
Y is phenyl optionally substituted with 1-5 independent halogen, —CN, NO$_2$, —C$_{1-6}$alkyl, —C$_{1-6}$alkenyl, —C$_{1-6}$alkynyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(=NR$^1$)R$^2$, or —C(=NOR$^1$)R$^2$ substituents, wherein optionally two substituents are combined to form a cycloalkyl or heterocycloalkyl ring fused to Y; wherein the —C$_{1-6}$alkyl substituent, cycloalkyl ring, or heterocycloalkyl ring each optionally is further substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) groups.

4. The compound of claim 1 wherein:
Y is 2-pyridyl optionally substituted with 1-4 independent halogen, —CN, NO$_2$, —C$_{1-6}$alkyl, —C$_{1-6}$alkenyl, —C$_{1-6}$alkynyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(=NR$^1$)R$^2$, or —C(=NOR$^1$)R$^2$ substituents, wherein optionally two substituents are combined to form a cycloalkyl or heterocycloalkyl ring fused to Y; wherein the —C$_{1-6}$alkyl substituent, cycloalkyl ring, or heterocycloalkyl ring each optionally is further substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) groups.

5. The compound of claim 4 wherein:
X is pyridyl optionally substituted with 1-4 independent halogen, —CN, NO$_2$, —C$_{1-6}$alkyl, —C$_{1-6}$alkenyl, —C$_{1-6}$alkynyl, 1, NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(NR$^1$)R$^2$, or —C(=NOR$^1$)R$^2$ substituents, wherein optionally two substituents are combined to form a cycloalkyl or heterocycloalkyl ring fused to X; wherein the —C$_{1-6}$alkyl substituent, cycloalkyl ring, or heterocycloalkyl ring each optionally is further substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) groups.

6. The compound of claim 1 wherein:
X is phenyl optionally substituted with 1-5 independent halogen, —CN, NO$_2$, —C$_{1-6}$alkyl, —C$_{1-6}$alkenyl, —C$_{1-6}$alkynyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$_2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(=NR$^1$)R$^2$, or —C(=NOR$^1$)R$^2$substituents, wherein optionally two substituents are combined to form a cycloalkyl or heterocycloalkyl ring fused to X; wherein the —C$_{1-6}$alkyl substituent, cycloalkyl ring, or heterocycloalkyl ring each optionally is further substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) groups.

7. The compound of claim 6 wherein:
Y is 2-pyridyl optionally substituted with 1-4 independent halogen, —CN, NO$_2$, —C$_{1-6}$alkyl, —C$_{1-6}$alkenyl, —C$_{1-6}$alkynyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(=NR$^1$)R$^2$, or —C(=NOR$^1$)R$^2$substituents, wherein optionally two substituents are combined to form a cycloalkyl or heterocycloalkyl ring fused to Y; wherein the —C$_{1-6}$alkyl substituent, cycloalkyl ring, or heterocycloalkyl ring each optionally is further substituted with 1-5 independent halogen, —Cn, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) groups.

8. The compound of claim 1 wherein:
Y is 1,3-thiazol-2-yl optionally substituted with 1-2 independent halogen, —CN, NO$_2$, —C$_{1-6}$alkyl, —C$_{1-6}$alkenyl, —C$_{1-6}$alkynyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(=NR$^1$)R$^2$, or —C(=NOR$^1$)R$^2$substituents, wherein optionally two substituents are combined to form a cycloalkyl or heterocycloalkyl ring fused to Y; wherein the —C$_{1-6}$ alkyl substituent, cycloalkyl ring, or heterocycloalkyl ring each optionally is further substituted with 1-5 independent halogen, —Cn, C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) groups.

9. The compound of claim 8 wherein:
X is phenyl optionally substituted with 1-5 independent halogen, —Cn, NO$_2$, —C$_{1-6}$alkyl, —C$_{1-6}$alkenyl, —C$_{1-6}$alkynyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(=NR$^1$)R$^2$, or —C(=NOR$^1$)

R² substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups.

10. The compound of claim 1 wherein:

Y is pyrazolyl optionally substituted with 1-3 independent halogen, —Cn, $NO_2$, —$C_{1-6}$alkyl, —$C_{1-6}$alkenyl, —$C_{1-6}$alkynyl, —$OR^1$, —$NR^1R^2$, —$C(=NR^1)NR^2R^3$, —$N(=NR^1)NR^2R^3$, —$NR^1COR_2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —$C(=NR^1)R^2$, or —$C(=NOR^1)$ R² substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —Cn, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups.

11. The compound of claim 10 wherein:

X is phenyl optionally substituted with 1-5 independent halogen, —Cn, $NO_2$, —$C_{1-6}$alkyl, —$C_{1-6}$alkenyl, —$C_{1-6}$alkynyl, —$OR^1$, —$NR^1R^2$, —$C(=NR^1)NR^2R^3$, —$N(=NR^1)NR^2R^3$, —$NR^1COR_2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —$C(=NR^1)R^2$, or —$C(=NOR^1)$ R² substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —Cn, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups.

12. A compound which is selected from the group consisting of:
- 3-(1-pyridin-2-yl-1H-pyrrol-3-yl)benzonitrile;
- 2-[3-(3-chlorophenyl)-1H-pyrrol-1-yl]pyridine;
- 2-[3-(3-methoxyphenyl)-1H-pyrrol-1-yl]pyridine;
- 3-(3-pyridin-2-yl-1H-pyrrol-1-yl)benzonitrile;
- 2-{1-[3-(trifluoromethyl)phenyl]-1H-pyrrol-3-yl}pyridine;
- 2-[1-(3,5-dichlorophenyl)-1H-pyrrol-3-yl]pyridine;
- 2-[1-(3-methylphenyl)-1H-pyrrol-3-yl]pyridine;
- 2-[1-(3-methoxyphenyl)-1H-pyrrol-3-yl]pyridine;
- 3-[3-(1,3-thiazol-2-yl)-1H-pyrrol-1-yl]benzonitrile;
- 3-fluoro-5-(3-pyridin-2-yl-1H-pyrrol-1-yl)benzonitrile;
- 3-(3-bromo-4-pyridin-2-yl-1H-pyrrol-1-yl)-5-fluorobenzonitrile;
- 3-fluoro-5-(3-methyl-4-pyridin-2-yl-1H-pyrrol-1-yl)benzonitrile;
- 3-(3-chloro-4-pyridin-2-yl-1H-pyrrol-1-yl)-5-fluorobenzonitrile;
- 3-fluoro-5-[3-(1H-pyrazol-1-yl)-1H-pyrrol-1-yl]benzonitrile;
- 2-chloro-6-(3-pyridin-2-yl-1H-pyrrol-1-yl)pyridine;
- 2-(pyridin-3-yloxy)-6-(3-pyridin-2-yl-1H-pyrrol-1-yl)pyridine;
- 2-chloro-4-methyl-6-(3-pyridin-2-yl-1H-pyrrol-1-yl)pyridine;
- 3-chloro-5-(3-pyridin-2-yl-1H-pyrrol-1-yl)benzonitrile;
- 2-{1-[3-fluoro-5-(pyridin-3-yloxy)phenyl]-1H-pyrrol-3-yl}pyridine;
- 3-bromo-5-(3-pyridin-2-yl-1H-pyrrol-1-yl)benzonitrile;
- 3-methyl-5-(3-pyridin-2-yl-1H-pyrrol-1-yl)benzonitrile;
- 3-fluoro-5-[3-(1,3-thiazol-2-yl)-1H-pyrrol-1-yl]benzonitrile;

or a pharmaceutically acceptable salt thereof.

13. A pharmaceutical composition comprising the compound of claim 1, or a pharmaceutically acceptable salt thereof, and a pharmaceutically acceptable carrier.

14. A pharmaceutical composition comprising the compound of claim 12, or a pharmaceutically acceptable salt thereof, and a pharmaceutically acceptable carrier.

15. A method of treatment or prevention of pain comprising the step of administering a therapeutically effective amount or a prophylactically effective amount of the compound of claim 1 or a pharmaceutically acceptable salt thereof.

16. A method of treatment or prevention of a pain disorder wherein the pain disorder is acute pain, persistent pain, chronic pain, inflammatory pain or neuropathic pain, comprising administering a therapeutically effective amount or a prophylactically effective amount of the compound of claim 1 or a pharmaceutically acceptable salt thereof.

* * * * *